(12) United States Patent
Catalano

(10) Patent No.: US 11,918,502 B2
(45) Date of Patent: Mar. 5, 2024

(54) BI-FLOW NASAL STENT

(71) Applicant: Peter Catalano, Watertown, MA (US)

(72) Inventor: Peter Catalano, Watertown, MA (US)

( * ) Notice: Subject to any disclaimer, the term of this patent is extended or adjusted under 35 U.S.C. 154(b) by 0 days.

(21) Appl. No.: 17/221,455

(22) Filed: Apr. 2, 2021

(65) Prior Publication Data

US 2021/0307951 A1 Oct. 7, 2021

Related U.S. Application Data

(60) Provisional application No. 63/028,189, filed on May 21, 2020, provisional application No. 63/003,967, filed on Apr. 2, 2020.

(51) Int. Cl.
*A61F 5/08* (2006.01)
*A61F 5/05* (2006.01)

(52) U.S. Cl.
CPC ..................................... *A61F 5/05* (2013.01)

(58) Field of Classification Search
CPC .. A61F 5/08; A61F 5/56; A61F 11/006; A61F 11/00; A61F 11/08; A61F 11/085
See application file for complete search history.

(56) References Cited

U.S. PATENT DOCUMENTS

| | | |
|---|---|---|
| 1,256,188 A | 2/1918 | Wilson |
| 5,665,104 A | 9/1997 | Lee |
| 5,775,335 A | 7/1998 | Seal |
| 5,895,409 A | 4/1999 | Mehdizadeh |
| D430,667 S | 9/2000 | Rome |
| D438,967 S | 3/2001 | Alpers |
| D451,193 S | 11/2001 | McCormick |
| 6,564,800 B1 | 5/2003 | Olivares |

(Continued)

FOREIGN PATENT DOCUMENTS

| | | |
|---|---|---|
| DE | 9403621 | 7/1994 |
| EP | 2387978 | 11/2011 |

(Continued)

*Primary Examiner* — Majid Jamialahmadi
(74) *Attorney, Agent, or Firm* — Pandiscio & Pandiscio

(57) ABSTRACT

A bi-flow nasal stent comprising: first and second tube-like elements; and a bridge connecting the first and second tube-like elements; wherein each of the first and second tube-like elements comprises a distal end, a proximal end, and a lumen extending therebetween, and further wherein each of the first and second tube-like elements comprises top side, a medial side, a bottom side, and a lateral side collectively forming the tube-like element; wherein the bridge connects the proximal end of the medial side of the first tube-like element to the proximal end of the medial side of the second tube-like element; and wherein each of the first and second tube-like elements comprises first and second V-shaped cutouts at the distal end of the tube-like element, with the first V-shaped cutout extending proximally in the top side of the tube-like element and the second V-shaped cutout extending proximally in the bottom side of the tube-like element, with the first and second V-shaped cutouts being diametrically opposed to one another so as to divide each of the tube-like elements into a medial side portion and a lateral side portion, with the medial side portion and the lateral side portion being connected together by a pair of diametrically-opposed connecting elements.

18 Claims, 24 Drawing Sheets

(56) References Cited

U.S. PATENT DOCUMENTS

| | | |
|---|---|---|
| D572,361 S | 7/2008 | Noce |
| D575,397 S | 8/2008 | Noce |
| D576,726 S | 9/2008 | Maxwell |
| 7,918,224 B2 | 4/2011 | Dolezal et al. |
| D652,518 S | 1/2012 | Jensen |
| D670,382 S | 11/2012 | Noce et al. |
| D683,015 S | 5/2013 | Zisser |
| D713,031 S | 9/2014 | McCormick |
| D726,312 S | 4/2015 | Johnson |
| D737,965 S | 9/2015 | Bende |
| 2002/0177871 A1 | 11/2002 | Santin |
| 2003/0195552 A1 | 10/2003 | Santin |
| 2004/0147954 A1 | 7/2004 | Wood |
| 2006/0085027 A1 | 4/2006 | Santin et al. |
| 2009/0054923 A1* | 2/2009 | Benson ............ A61F 5/08 606/199 |
| 2009/0093840 A1* | 4/2009 | MacDonald ......... A61M 29/00 606/199 |
| 2010/0031965 A1 | 2/2010 | Söderberg |
| 2012/0318279 A1 | 12/2012 | Yamada et al. |
| 2014/0246023 A1 | 9/2014 | Maryankaa |
| 2014/0261459 A1* | 9/2014 | Santelli, Jr. ............ A61L 9/16 53/473 |
| 2014/0326244 A1 | 11/2014 | Orts Paya et al. |
| 2020/0206547 A1* | 7/2020 | Hellman ............ A62B 23/06 |

FOREIGN PATENT DOCUMENTS

| | | |
|---|---|---|
| EP | 2567735 | 3/2013 |
| JP | 2007195604 | 8/2007 |
| WO | WO2004069110 | 8/2004 |

* cited by examiner

BI-FLOW NASAL STENT

REFERENCE TO PENDING PRIOR PATENT APPLICATIONS

This patent application:
(i) claims benefit of prior U.S. Provisional Patent Application Ser. No. 63/003,967, filed Apr. 2, 2020 by Peter Catalano for BI-FLOW NASAL STENT; and
(ii) claims benefit of prior U.S. Provisional Patent Application Ser. No. 63/028,189, filed May 21, 2020 by Peter Catalano for BI-FLOW NASAL STENT.

The two (2) above-identified patent applications are hereby incorporated herein by reference.

FIELD OF THE INVENTION

This invention relates to internal and external nasal valve collapse in general, and more particularly to a nasal valve stent for treating nasal valve collapse.

BACKGROUND OF THE INVENTION

The human nose has two channels, one on each of the left and right sides of the nose, with both channels leading to a single nasal cavity (see FIG. 1). The two channels are separated by the septum. Each of the channels has an external nasal valve (at the entrance to the nose) and an internal nasal valve (the narrowest area of each channel, located interior of the external nasal valve).

During normal inhalation through the nose, inspired air flows through the two channels, going past the external nasal valves and then past the internal nasal valves before entering the nasal cavity. As the air enters the nasal cavity, the air generally fills the space, primarily following an upper air pathway A and secondarily following a lower air pathway B (see FIG. 2). On the other hand, during normal exhalation through the nose, expired air generally exits the nasal cavity primarily following the lower air pathway B and secondarily following the upper air pathway A (see FIG. 3). The air flows outwards through the two channels, going past the internal nasal valves and then the external nasal valves.

The air flow through these channels may be compromised by external and/or internal nasal valve collapse, i.e., by the physical collapse of a patient's nostril(s). This condition, which is quite common, can be traced to a variety of causes including previous cosmetic rhinoplasty, nasal trauma, or congenital defects. However, this phenomenon also manifests itself to a lesser degree even in patients with normally developed noses when sniffing or inhaling deeply, as often occurs during exercise.

Patients afflicted with nasal valve collapse may experience increased resistance while breathing due to partial blockage of the channels and, in severe cases, the channels may be completely blocked. Any resistance to air flow is exacerbated during strenuous physical activity and sleep because these activities force the patient to increase the speed and/or volume of respiration which, in turn, increases nasal valve collapse (i.e., due to the Bernoulli Principle). In response to feeling resistance while breathing, a patient may compensate by breathing more through their mouth, however, this is a non-physiologic solution. Mouth-breathing can negatively affect dental health and cranio-facial development in children, and add to snoring, obstructive sleep apnea, and poor sleep quality in adults and children.

In order to combat nasal valve collapse, several methods of treatment and devices have been developed.

One such method of treatment is functional rhinoplasty to correct the anatomy of the nose, but this procedure is typically expensive and requires recovery, as with any surgical procedure.

Alternatively, a patient may opt to use skin-mounted adhesive nasal strips, which are inexpensive and non-invasive but are not particularly effective for patients with anatomical deformities. Additionally, many patients are allergic to the adhesive, and/or develop skin irritation from frequent nighttime use (due to the daily application and removal of the skin-mounted adhesive nasal strips).

A third alternative for patients suffering from nasal valve collapse is in-nostril nasal stents to physically dilate the nostrils. These devices typically comprise two tubular elements connected by a bridge. See FIG. 3A. The two tubular elements sit within the nasal channels and prevent the nostrils from collapsing. See FIG. 3B. These devices are inexpensive and easy to use, making them an attractive option. However, the nasal stents currently on the market are inadequate in that the tubular elements are generally cylindrically shaped and point upwards into the nasal cavity when in use, resulting in abnormal respiration. More specifically, during inhalation with these prior art nasal stents, air is directed into the upper air pathway A, but not into the lower air pathway B (see FIG. 4). During exhalation with these prior art nasal stents, air cannot easily escape the nasal cavity because the lower, more physiologic pathway for exhalation (Pathway B) is obstructed by the device (see FIG. 5). In addition, prior art tubular in-nostril nasal stents are substantially rigid tubes and they project relatively deep into the nostril, making them uncomfortable to wear for extended periods of time.

Additional prior art devices use firm, non-tubular plastic components with a spring-like design that sit within the nasal valve area and apply externally-directed pressure on the collapsing inner side walls of the nostril. See FIG. 5A. However, these devices are fairly rigid, and thus very uncomfortable when used for hours of use (as would be required during sleep).

Thus there is a need for a comfortable self-retaining nasal stent which dilates the nostrils of the nose and allows for inspired and expired air to flow in their natural pathways to maintain physiologic nasal breathing.

SUMMARY OF THE INVENTION

This and other objects of the present invention are addressed by the provision and use of a novel bi-flow nasal stent having a unique design.

More particularly, in accordance with the present invention, there is provided a new and improved bi-flow nasal stent generally comprising two tube-like elements which sit within the nasal channels and prevent the nostrils from collapsing. The two tube-like elements are connected by a bridge. Each tube-like element may also (optionally) have a nub on its top, proximal, medial zone, or at another location on the tube-like element. Significantly, the walls of the tube-like elements have a plurality of large "V-shaped" cutouts at their distal ends, specifically on the upper and lower portions, thus creating medial and lateral walls (sometimes hereinafter referred to as medial and lateral portions), with the medial portions and the lateral portions being connected together by a pair of diametrically-opposed connecting elements. In one preferred form of the invention, these diametrically-opposed connecting elements comprise spring hinges (e.g., resilient living hinges) which allow the medial portions and lateral portions to flexibly contour to the shape of one's nostril, with the medial portion applying a gentle force to the septum of the nose and the lateral portion applying a gentle force to the lateral side wall of the nostril.

During inhalation, air is allowed to flow into the nasal cavity through both the primary upper pathway A and the secondary lower pathway B, since the large "V-shaped" cutouts on the upper and lower portions of the tube-like elements allow the inspired air to disperse with more verticality. This is the correct, natural physiologic inspiration.

During exhalation, air is allowed to flow out of the nasal cavity through both the secondary upper pathway A and lower primary pathway B, since the large "V-shaped" cutouts on the upper and lower portions of the tube-like elements allow the expired air to enter the tube-like elements at a greater angle. This is the correct, natural physiologic exhalation.

In one preferred form of the invention, there is provided a bi-flow nasal stent comprising:
first and second tube-like elements; and
a bridge connecting the first and second tube-like elements;
wherein each of the first and second tube-like elements comprises a distal end, a proximal end, and a lumen extending therebetween, and further wherein each of the first and second tube-like elements comprises top side, a medial side, a bottom side, and a lateral side collectively forming the tube-like element;
wherein the bridge connects the proximal end of the medial side of the first tube-like element to the proximal end of the medial side of the second tube-like element; and
wherein each of the first and second tube-like elements comprises first and second V-shaped cutouts at the distal end of the tube-like element, with the first V-shaped cutout extending proximally in the top side of the tube-like element and the second V-shaped cutout extending proximally in the bottom side of the tube-like element, with the first and second V-shaped cutouts being diametrically opposed to one another so as to divide each of the tube-like elements into a medial side portion and a lateral side portion, with the medial side portion and the lateral side portion being connected together by a pair of diametrically-opposed connecting elements.

In another preferred form of the invention, there is provided a method for dilating the nostrils of a nose, the method comprising:
providing a bi-flow nasal stent comprising:
first and second tube-like elements; and
a bridge connecting the first and second tube-like elements;
wherein each of the first and second tube-like elements comprises a distal end, a proximal end, and a lumen extending therebetween, and further wherein each of the first and second tube-like elements comprises top side, a medial side, a bottom side, and a lateral side collectively forming the tube-like element;
wherein the bridge connects the proximal end of the medial side of the first tube-like element to the proximal end of the medial side of the second tube-like element; and
wherein each of the first and second tube-like elements comprises first and second V-shaped cutouts at the distal end of the tube-like element, with the first V-shaped cutout extending proximally in the top side of the tube-like element and the second V-shaped cutout extending proximally in the bottom side of the tube-like element, with the first and second V-shaped cutouts being diametrically opposed to one another so as to divide each of the tube-like elements into a medial side portion and a lateral side portion, with the medial side portion and the lateral side portion being connected together by a pair of diametrically-opposed connecting elements; and
positioning the first and second tube-like elements in the nostrils of the nose.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts and further wherein.

DETAILED DESCRIPTION OF THE INVENTION

Figure 1:
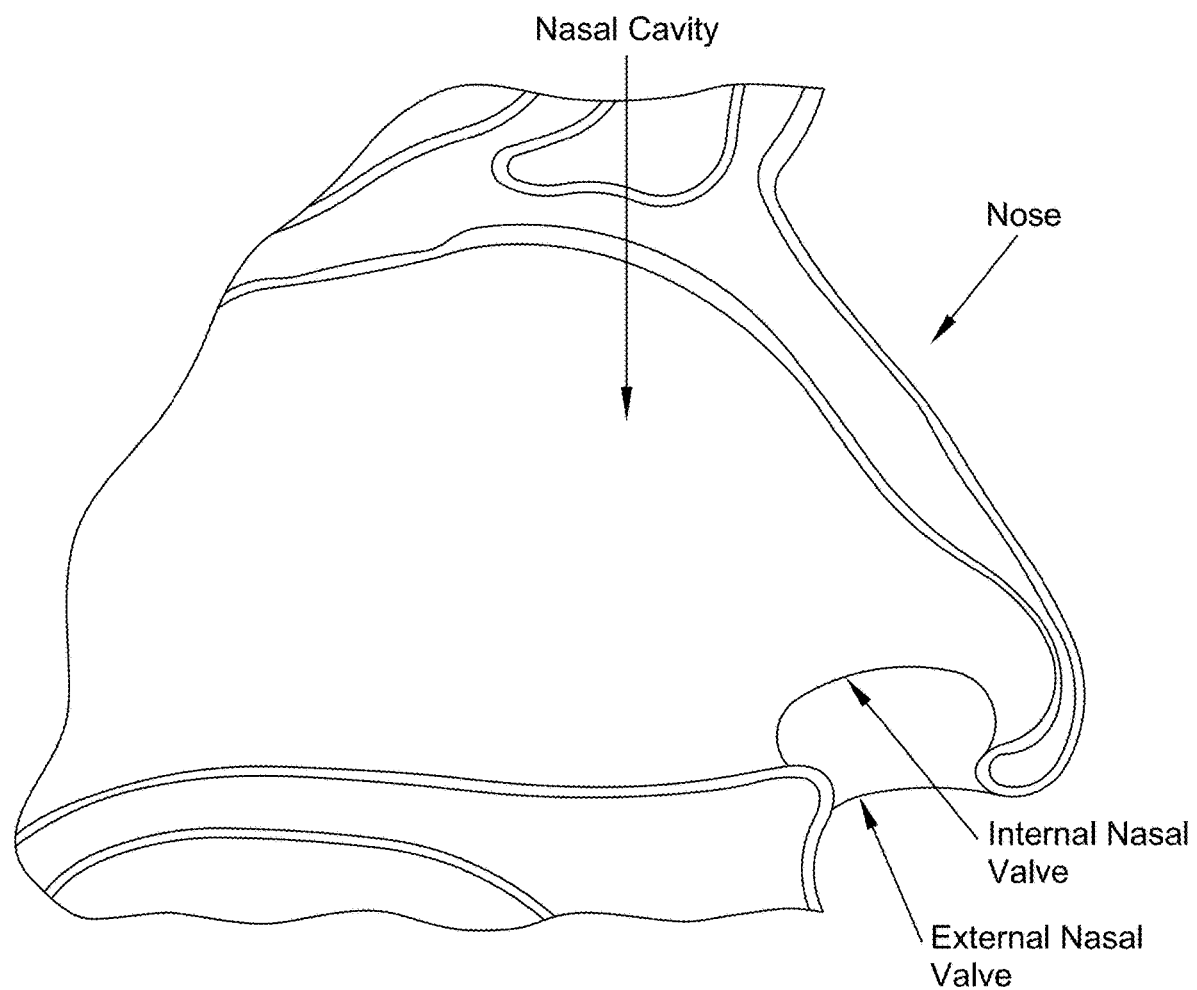
FIG. 1 is a schematic diagram showing the anatomy of a nose.
Figure 2:
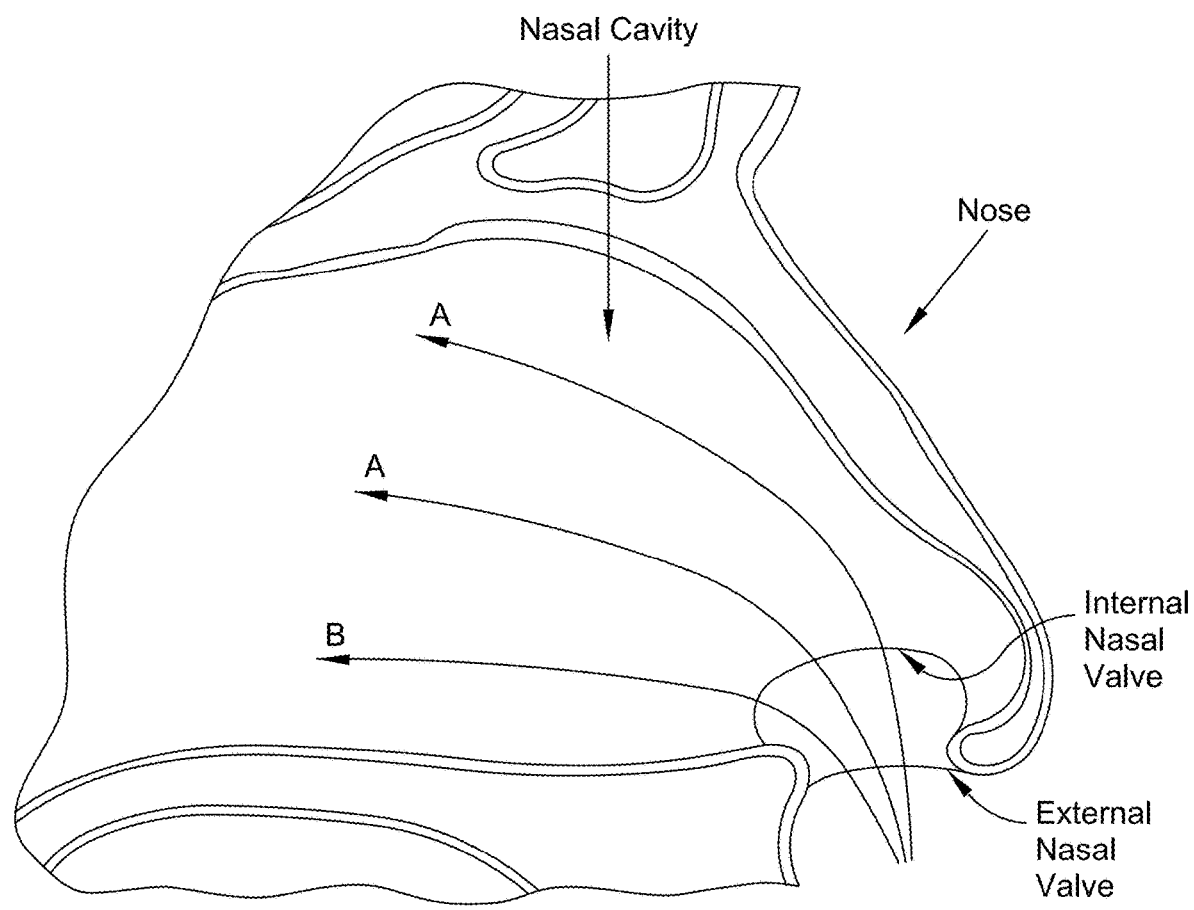
FIG. 2 is a schematic diagram showing the normal pathways of air inhaled through a nose, with the inhaled air primarily flowing through upper pathway A.
Figure 3:
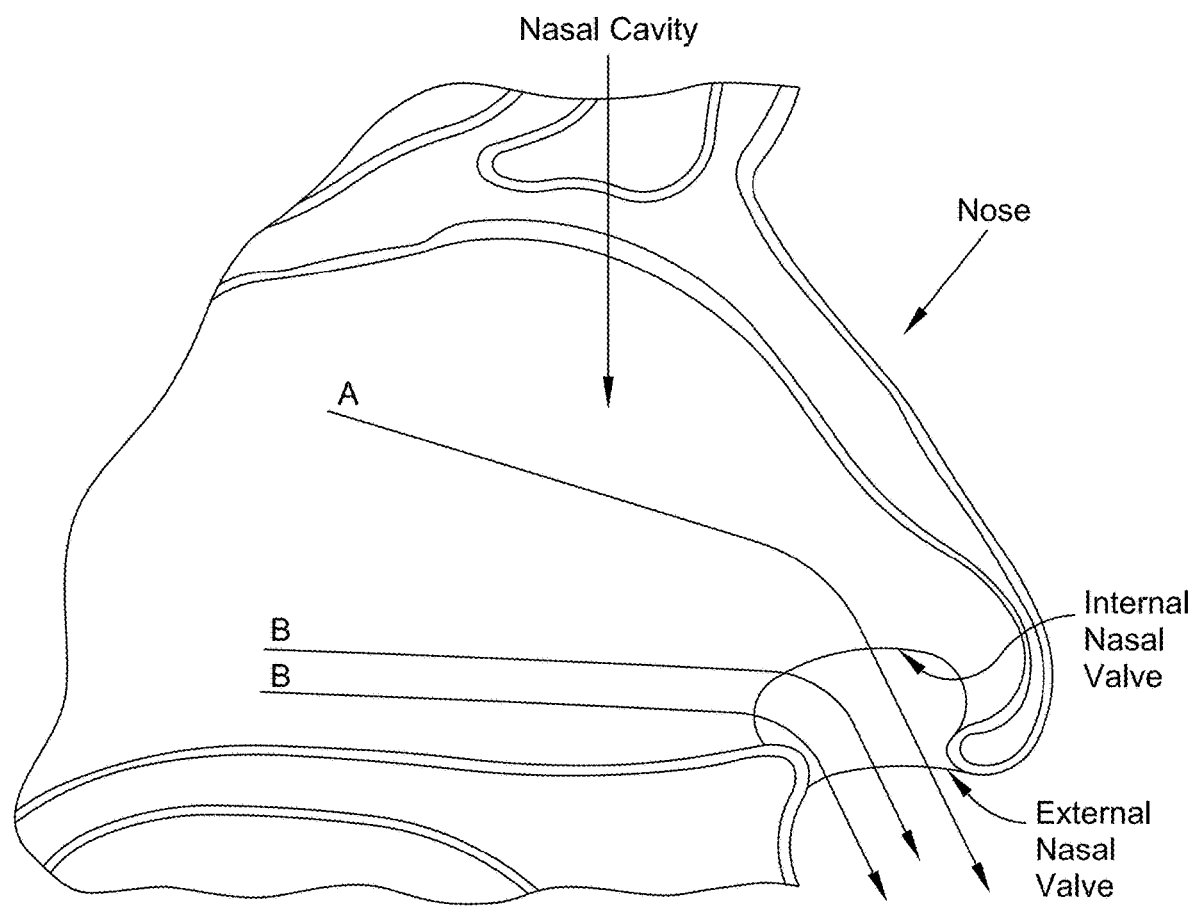
FIG. 3 is a schematic diagram showing the normal pathways of air exhaled through a nose, with the exhaled air primarily flowing via lower pathway B.
Figure 3A:
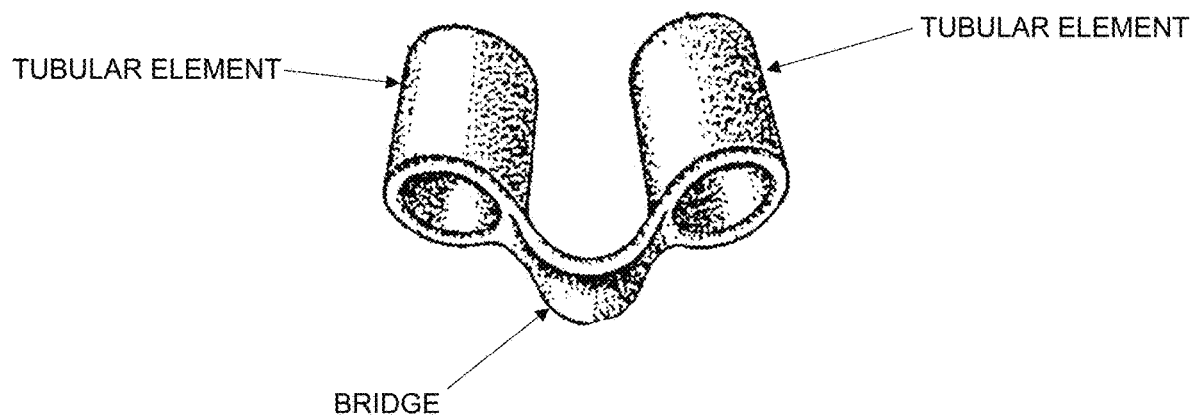
FIGS. 3A and 3B are schematic views showing a prior art in-nostril nasal stent.
Figure 3B:
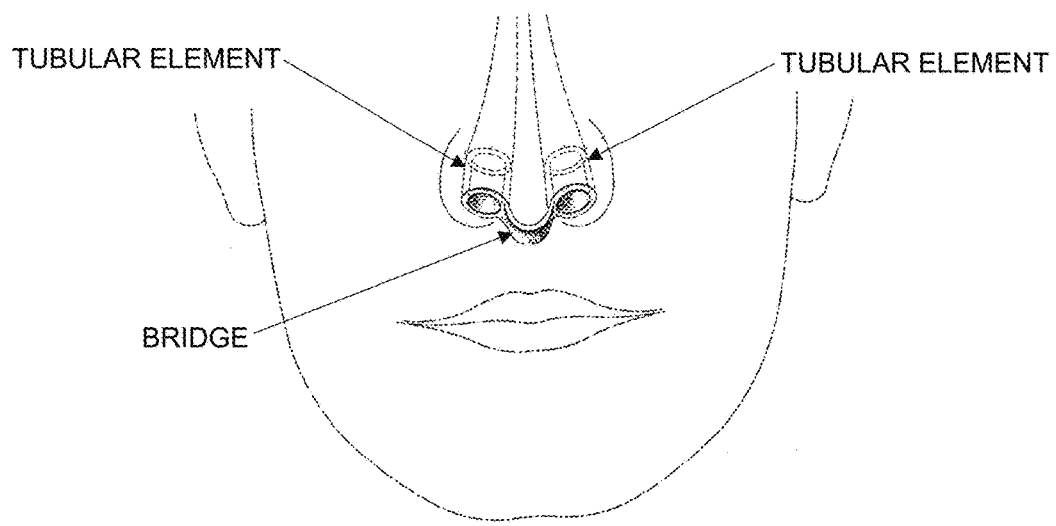
Figure 4:
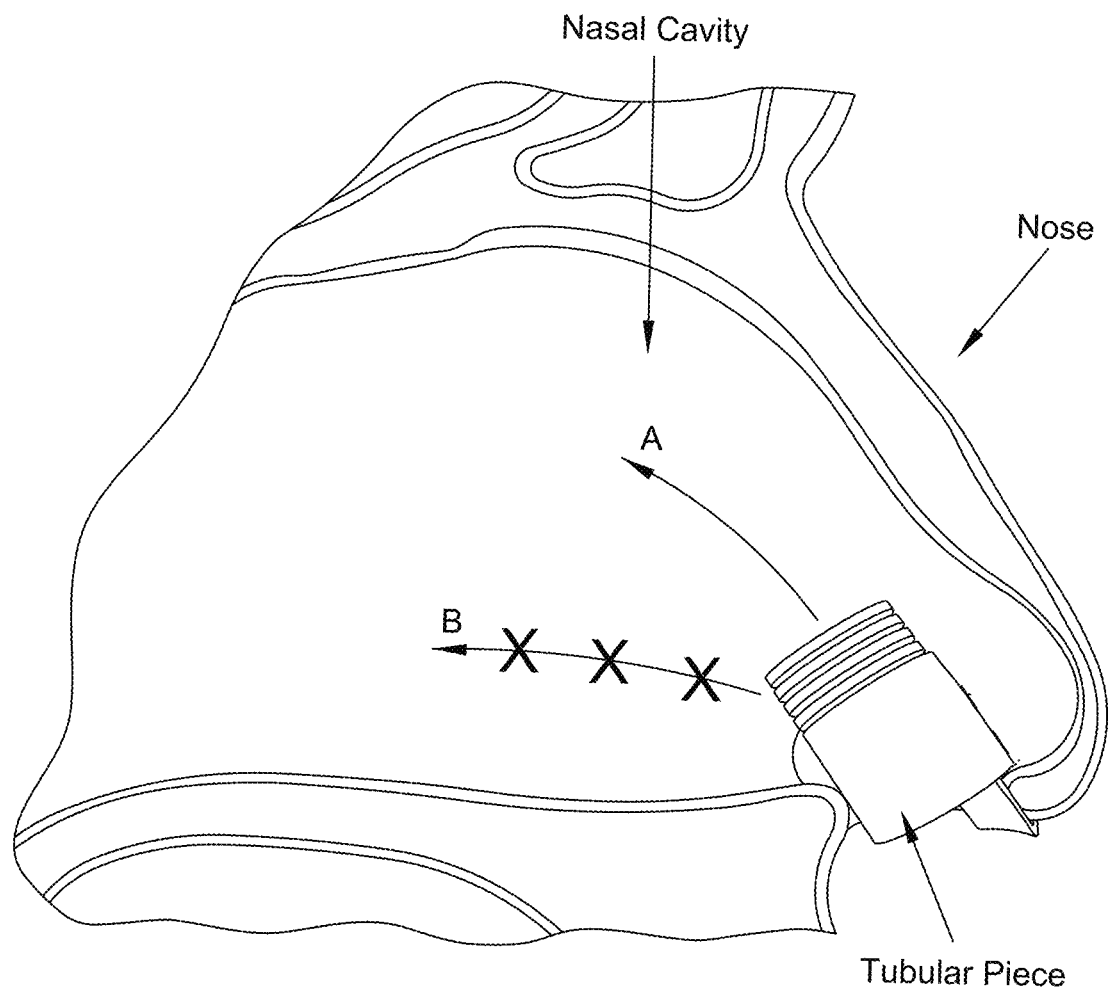
FIG. 4 is a schematic view showing a prior art nasal stent in use during inhalation, which blocks access to lower pathway B.
Figure 5:
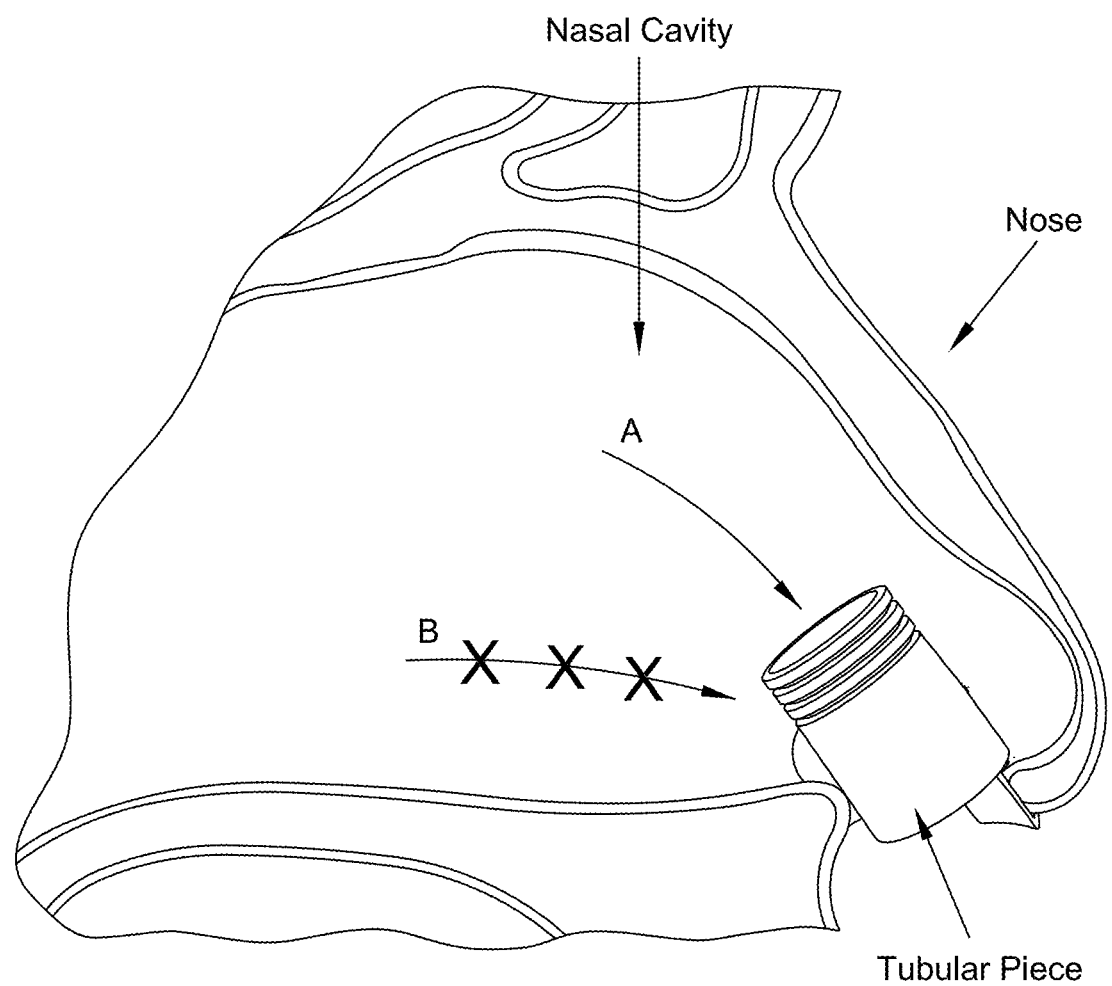
FIG. 5 is a schematic view showing a prior art nasal stent in use during exhalation, which blocks access to primary lower pathway B.
Figure 5A:
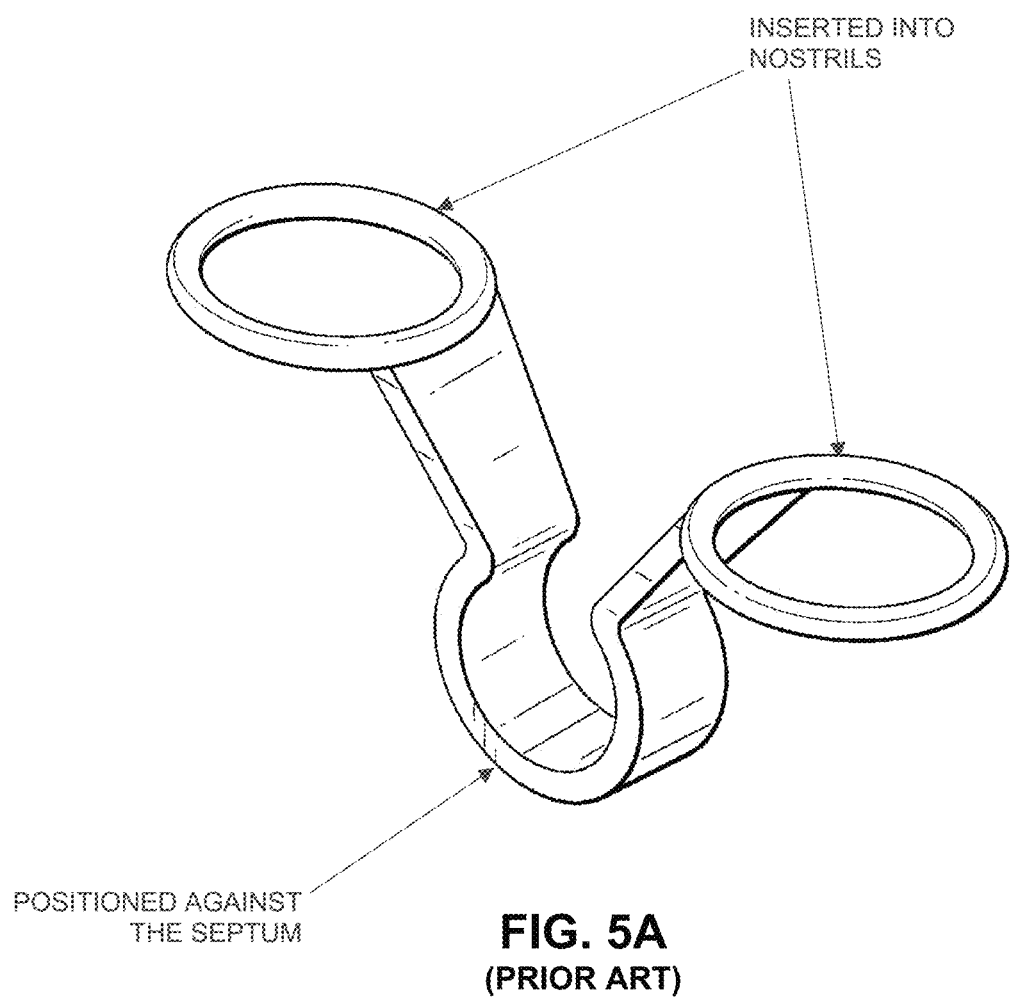
FIG. 5A is a schematic view showing another prior art device which sits within the nasal valve area and applies externally-directed pressure to collapsing inner side walls of the nostril.
Figure 6:
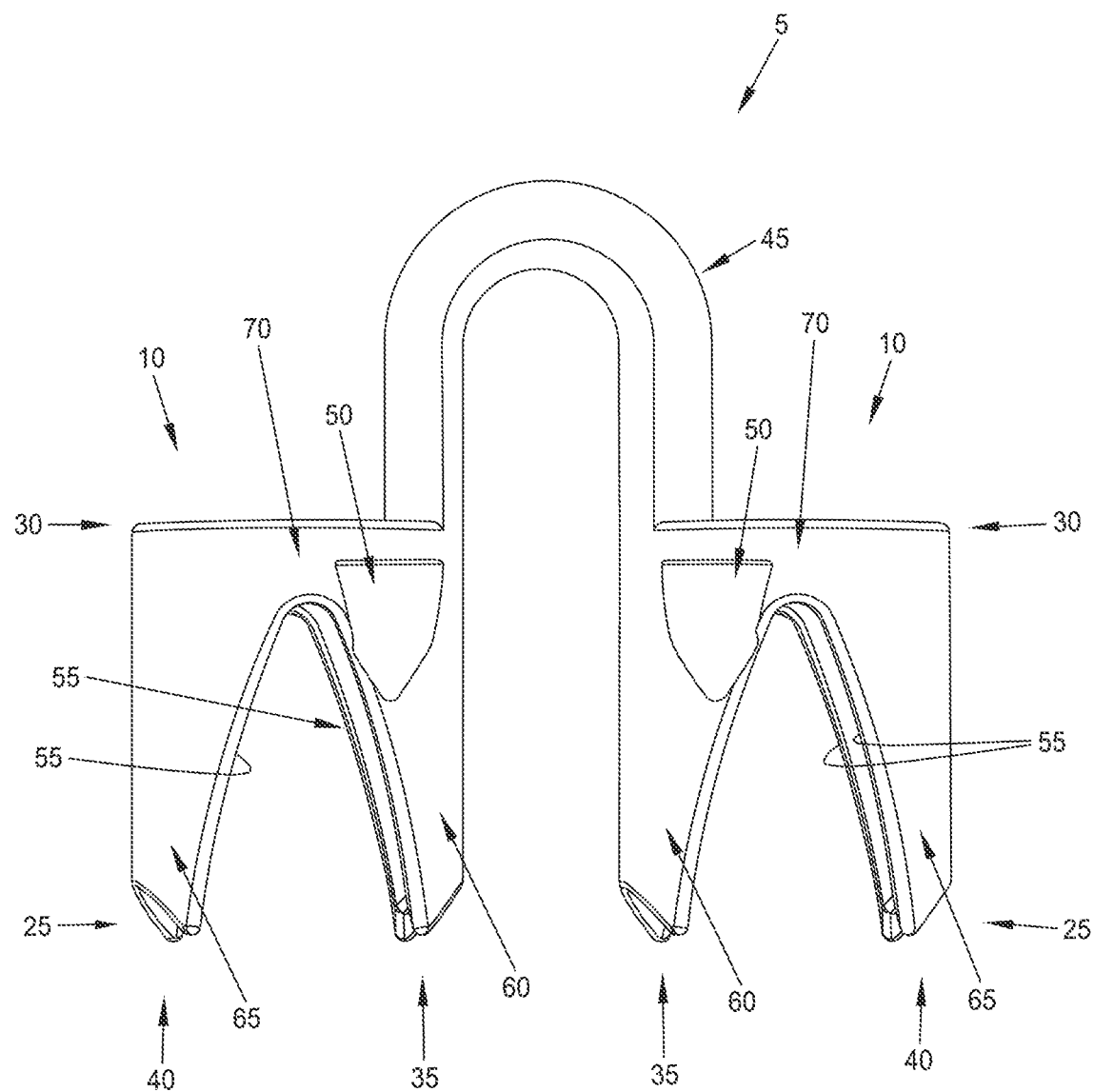
FIG. 6 is a top view of a novel bi-flow nasal stent.
Figure 7:
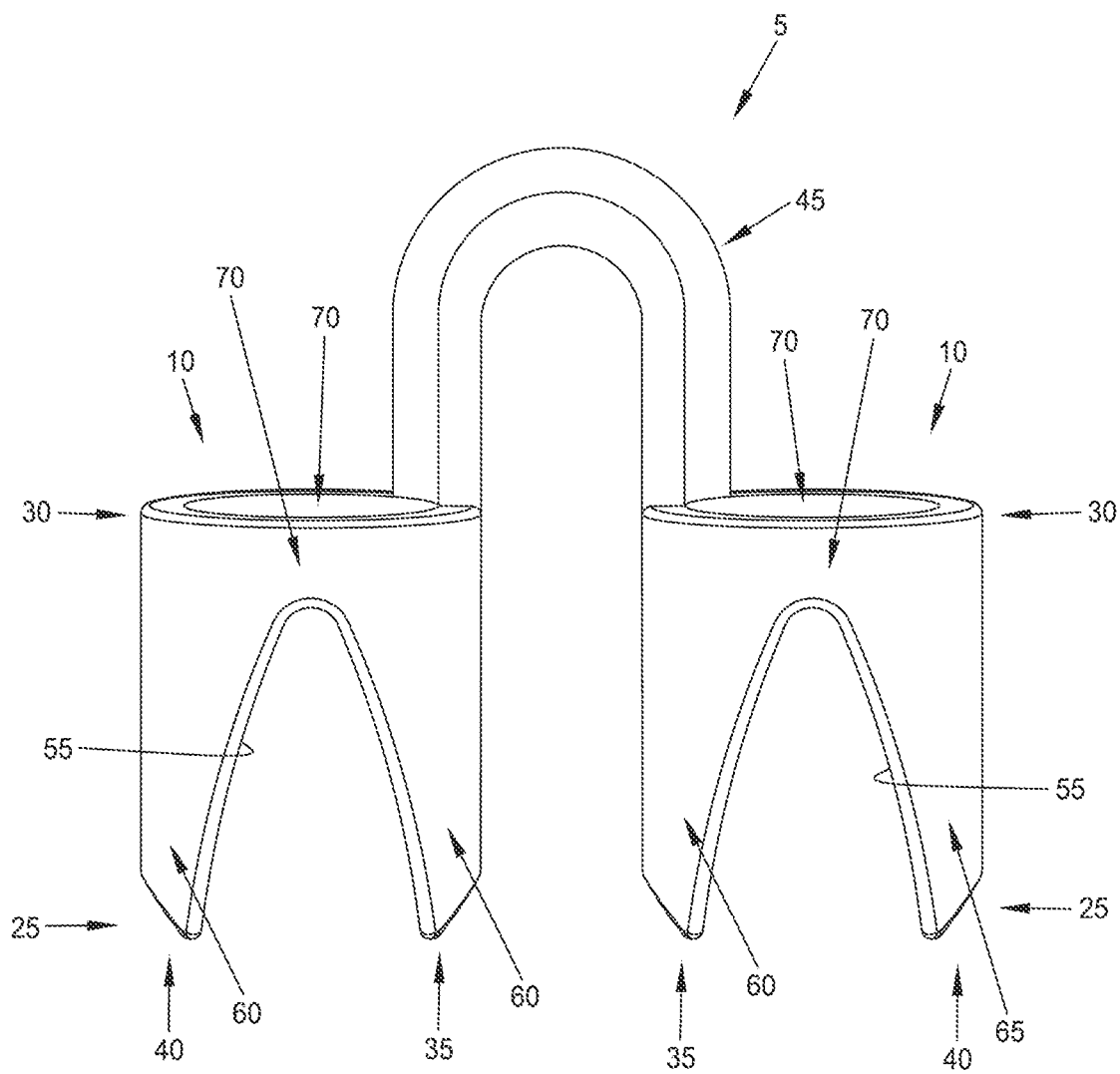
FIG. 7 is a bottom view of the novel bi-flow nasal stent of FIG. 6.
Figure 8:
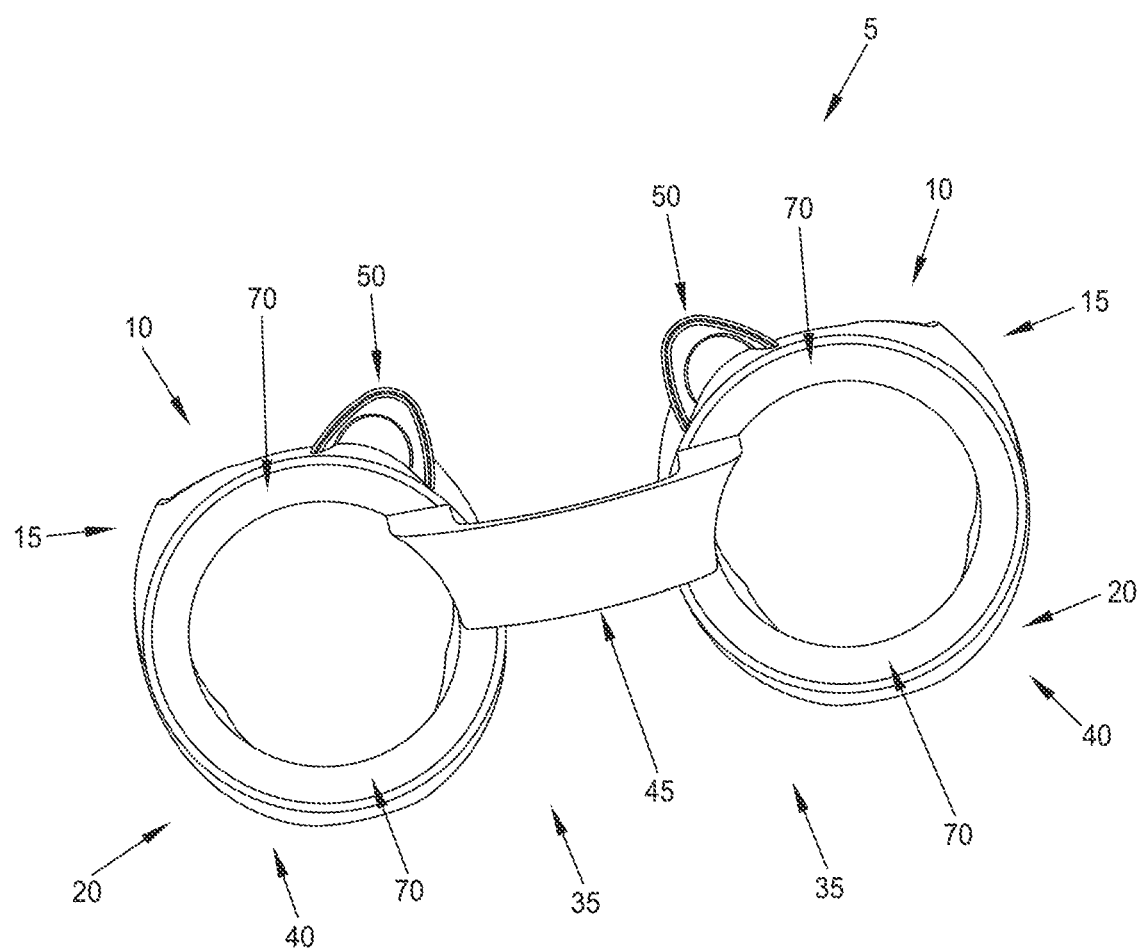
FIG. 8 is a proximal view of the novel bi-flow nasal stent of FIGS. 6 and 7.
Figure 9:
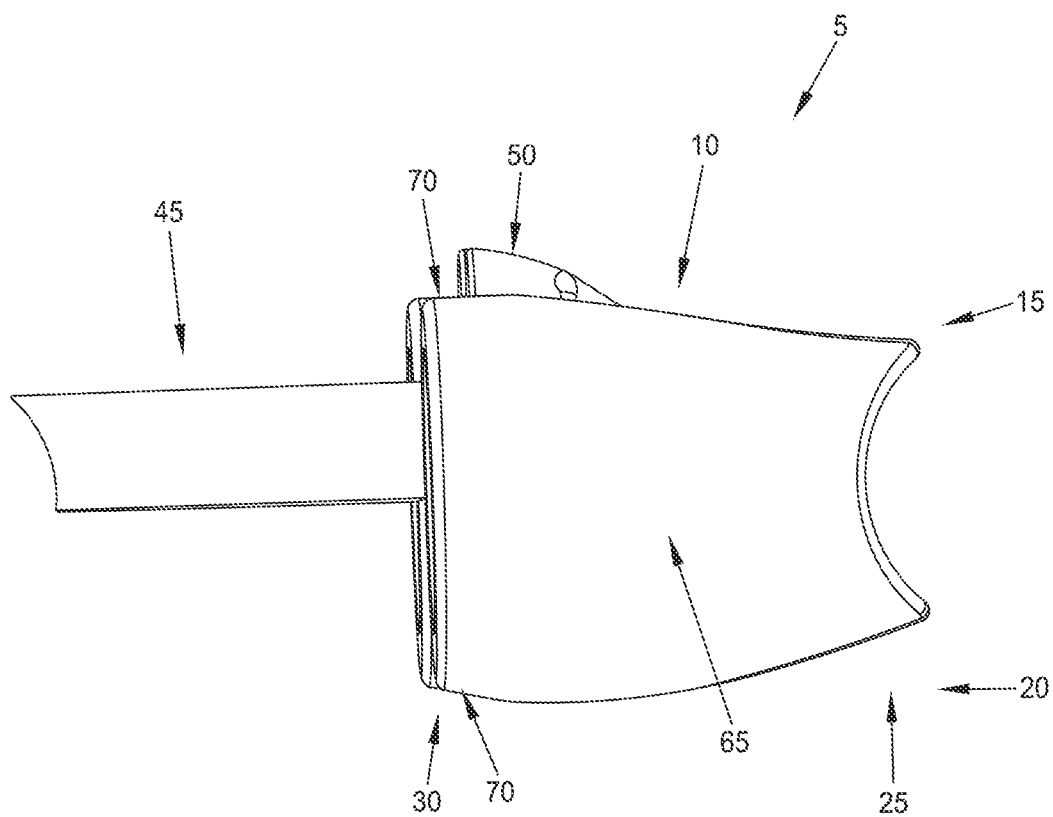
FIG. 9 is a side view of the novel bi-flow nasal stent of FIGS. 6-8.
Figure 10:
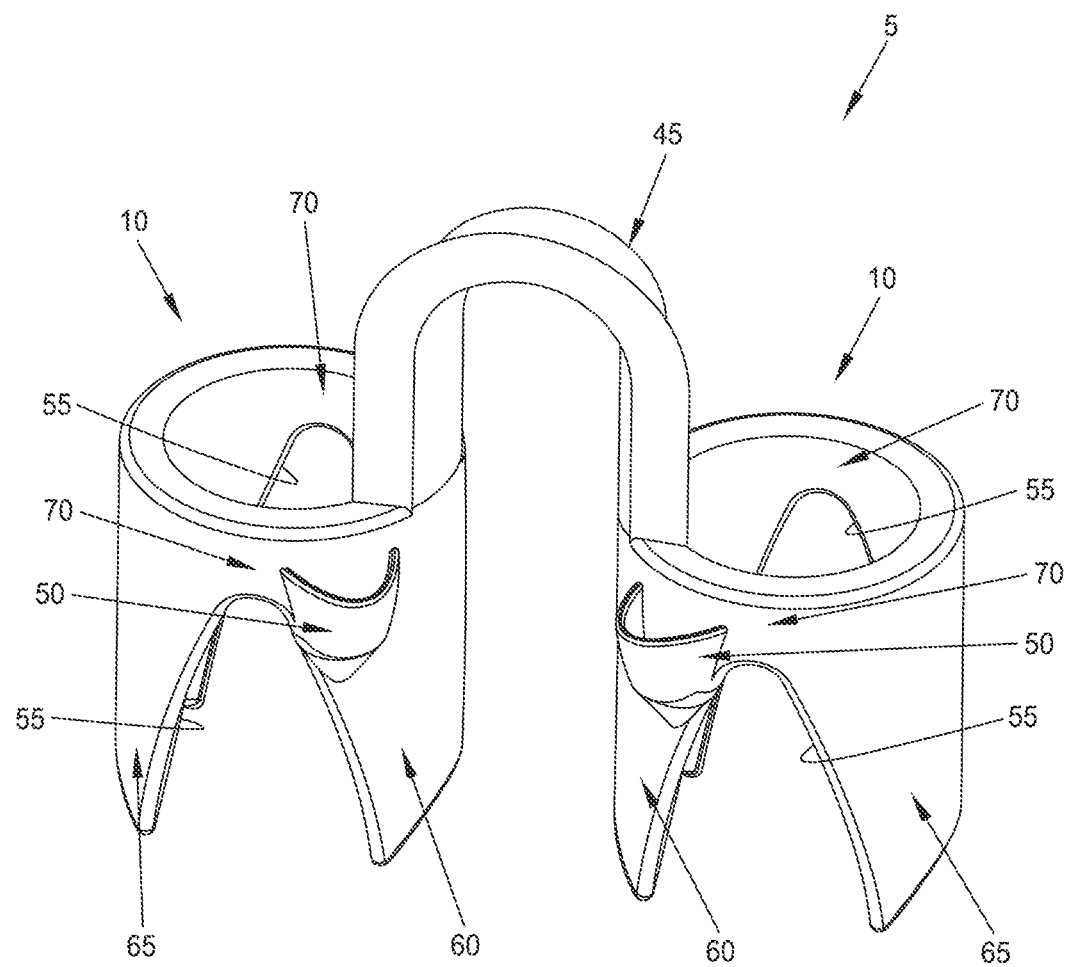
FIG. 10 is a proximal perspective view of the novel bi-flow nasal stent of FIGS. 6-9.
Figure 11:
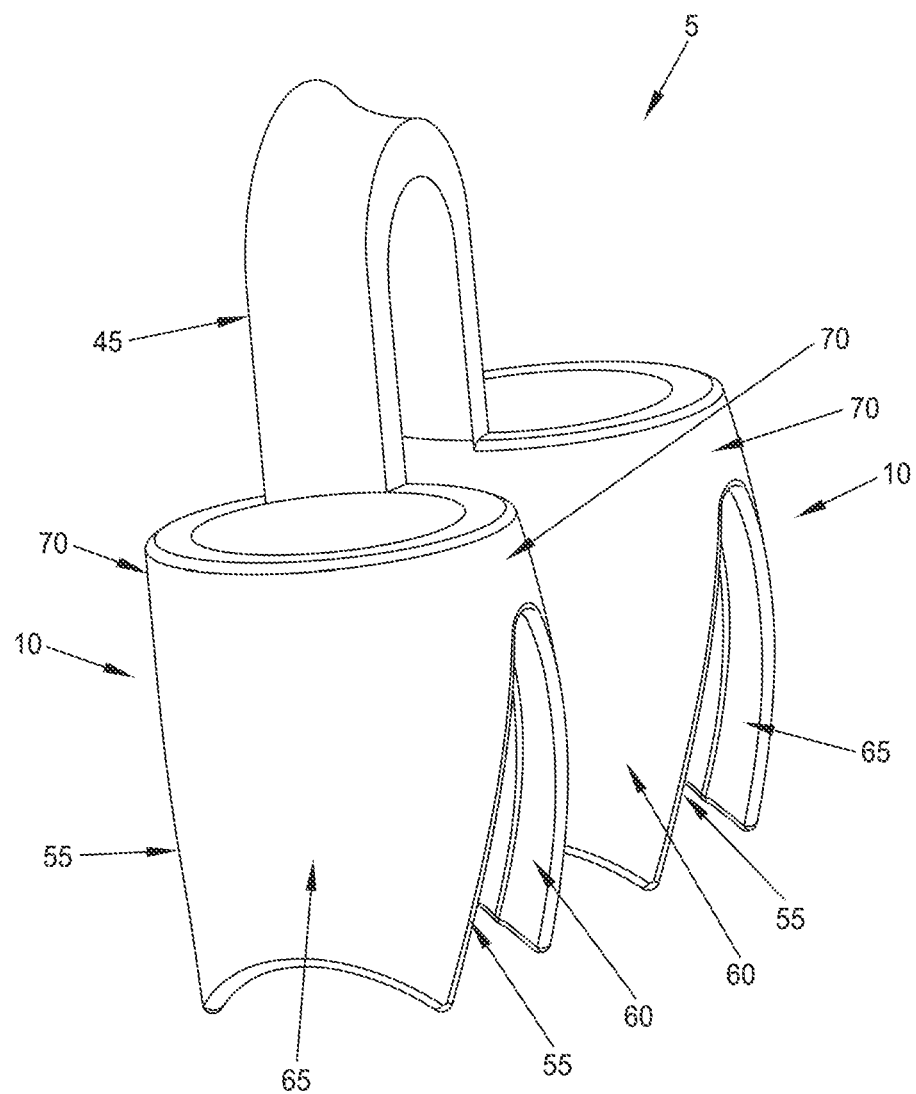
FIG. 11 is another perspective view of the novel bi-flow nasal stent of FIGS. 6-10.

The present invention comprises the provision and use of a novel bi-flow nasal stent which dilates the internal and external nasal valves and allows for inspired and expired air to flow in their natural physiologic pathways.

Looking now at FIGS. 6-11, there is shown a novel bi-flow nasal stent 5. Novel bi-flow nasal stent 5 generally comprises two tube-like elements 10 each having a top side 15, a bottom side 20, a distal end 25, a proximal end 30, a medial side 35 and a lateral side 40. Novel bi-flow nasal stent 5 further comprises a "U-shaped" bridge 45 which joins tube-like elements 10 on their proximal ends 30. Novel bi-flow nasal stent 5 may also (optionally) comprise nubs 50 on the top, proximal, medial areas of each of the tube-like elements 10 (or at another location on tube-like elements 10). Preferably the two tube-like elements 10, "U-shaped" bridge 45 and nubs 50 (if provided) are all formed integral with one another out of a relatively soft resilient material, e.g., a material soft enough to conform to the anatomy while still providing adequate support for the anatomy.

Significantly, novel bi-flow nasal stent 5 also comprises a plurality of large "V-shaped" cutouts 55 at distal ends 25 of tube-like elements 10, specifically on the top portions 15 and bottom portions 20 of tube-like elements 10. These large "V-shaped" cutouts 55 are preferably diametrically opposed to one another so as to divide each of the tube-like elements 10 into a medial side portion 60 and a lateral side portion 65, with the medial side portions 60 and the lateral side portions 65 being connected together by a pair of diametrically-opposed connecting elements 70. In one preferred form of the invention, these diametrically-opposed connecting portions 70 act as spring hinges (e.g., resilient living hinges) to allow the medial side portions 60 and the lateral side portions 65 to spring towards and away from one another, whereby to allow the two tube-like elements 10 to conform to the anatomy of the nostrils while still providing adequate support for the anatomy (i.e., adequate support for the nasal valves), with medial side portions 60 applying a gentle force to the septum of the nose and lateral side portions 65 applying a gentle force to the lateral side walls of the nostrils. In this respect it should be appreciated that providing support to the anatomy on the lateral sides of the nostrils is essential for maintaining patency in the nasal channels during respiration. Significantly, with the present invention, when tube-like elements 10 are disposed in the nostrils of the wearer, the lateral side portions 65 can compress towards the medial side portions 60 as needed in order to accommodate the anatomy, but as the lateral side portions 65 are increasingly compressed towards the medial side portions 60, the spring hinges of the diametrically-opposed connecting elements 70 provide the lateral side portions 65 with increasing resistance to the anatomy, whereby to provide excellent anatomical support (i.e., for the nasal valves) and prevent collapse of the nostril walls.

It should be appreciated that each of the tube-like elements 10 is relatively short, e.g., approximately 10 millimeters from distal end to proximal end, with the diametrically-opposed connecting elements 70 being significantly shorter, e.g., approximately 3 millimeters from distal end to proximal end. As a result, tube-like elements 10 of bi-flow nasal stent 5 sit in the wider, less-sensitive proximal portions of the nostrils so as to provide increased user comfort. It should also be appreciated that, as seen in (for example) FIG. 9, tube-like elements 10 have a smaller distal end 25 and a larger proximal end 30, and curved top and bottom sides 15, 20, so as to better fit in the nostrils.

In use, bi-flow nasal stent 5 has its tube-like elements 10 inserted, distal end first, into the nostrils of the patient. As tube-like elements 10 advance into the nostrils of the patient, the lateral and medial side portions 65, 60 can compress towards one another as needed so that tube-like elements 10 can seat comfortably and securely in the nostrils. Bi-flow nasal stent 5 can be advanced until bridge 45 approaches or engages the septum of the nose.

Figure 12:
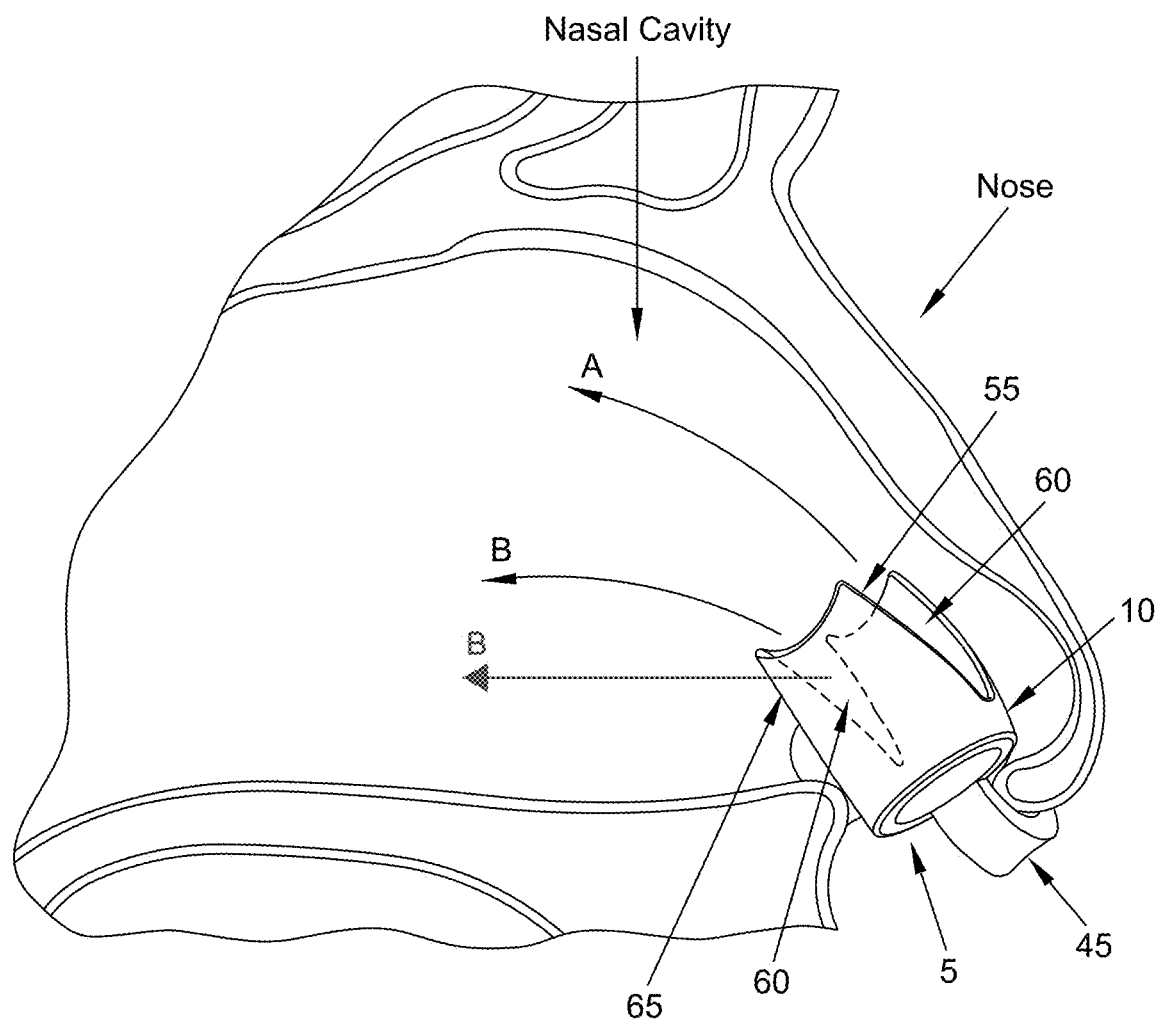
FIG. 12 is a schematic view showing the novel bi-flow nasal stent of the present invention in use during inhalation.
Figure 13:
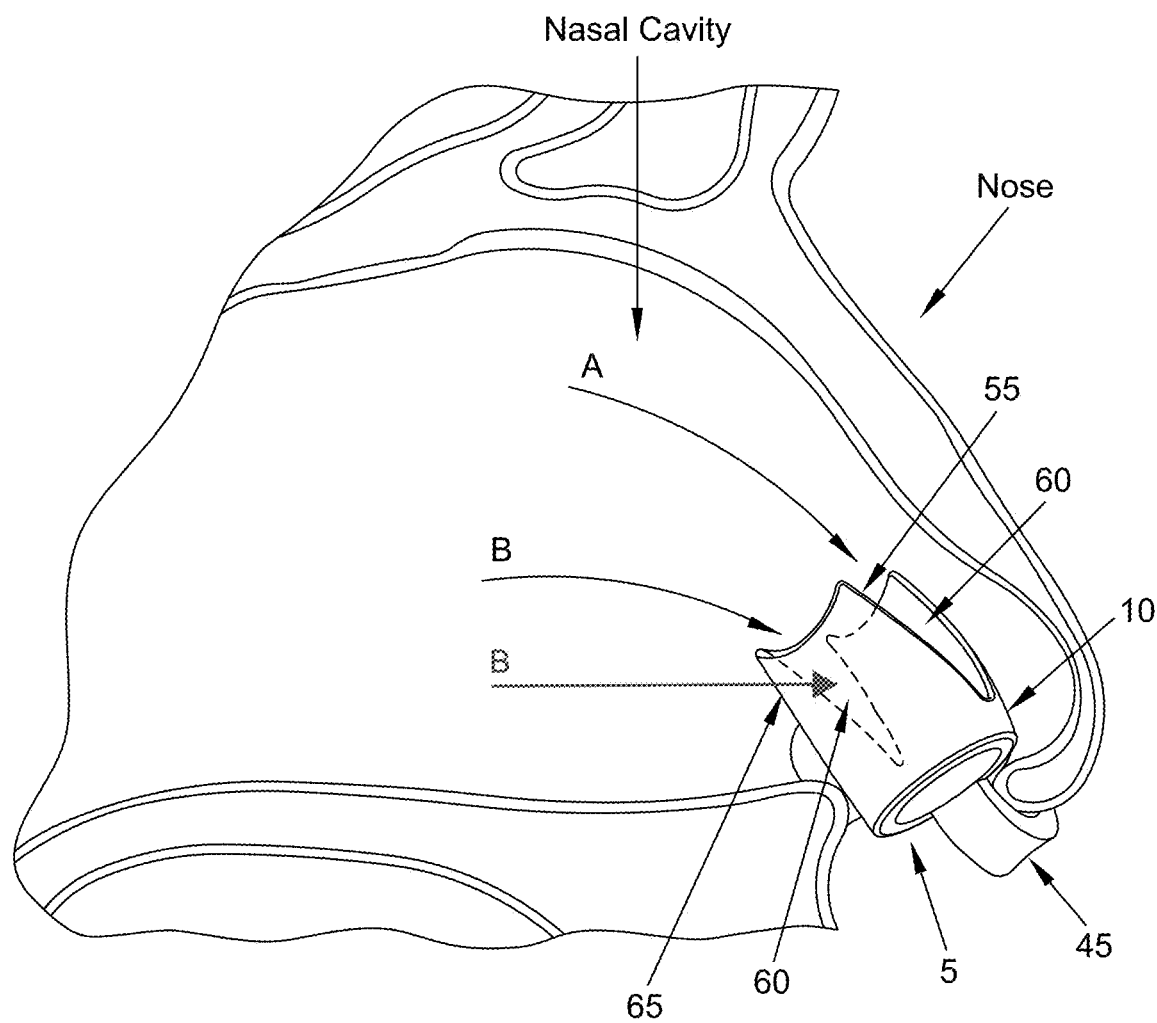
FIG. 13 is a schematic view showing the novel bi-flow nasal stent of the present invention in use during exhalation.
Figure 14:
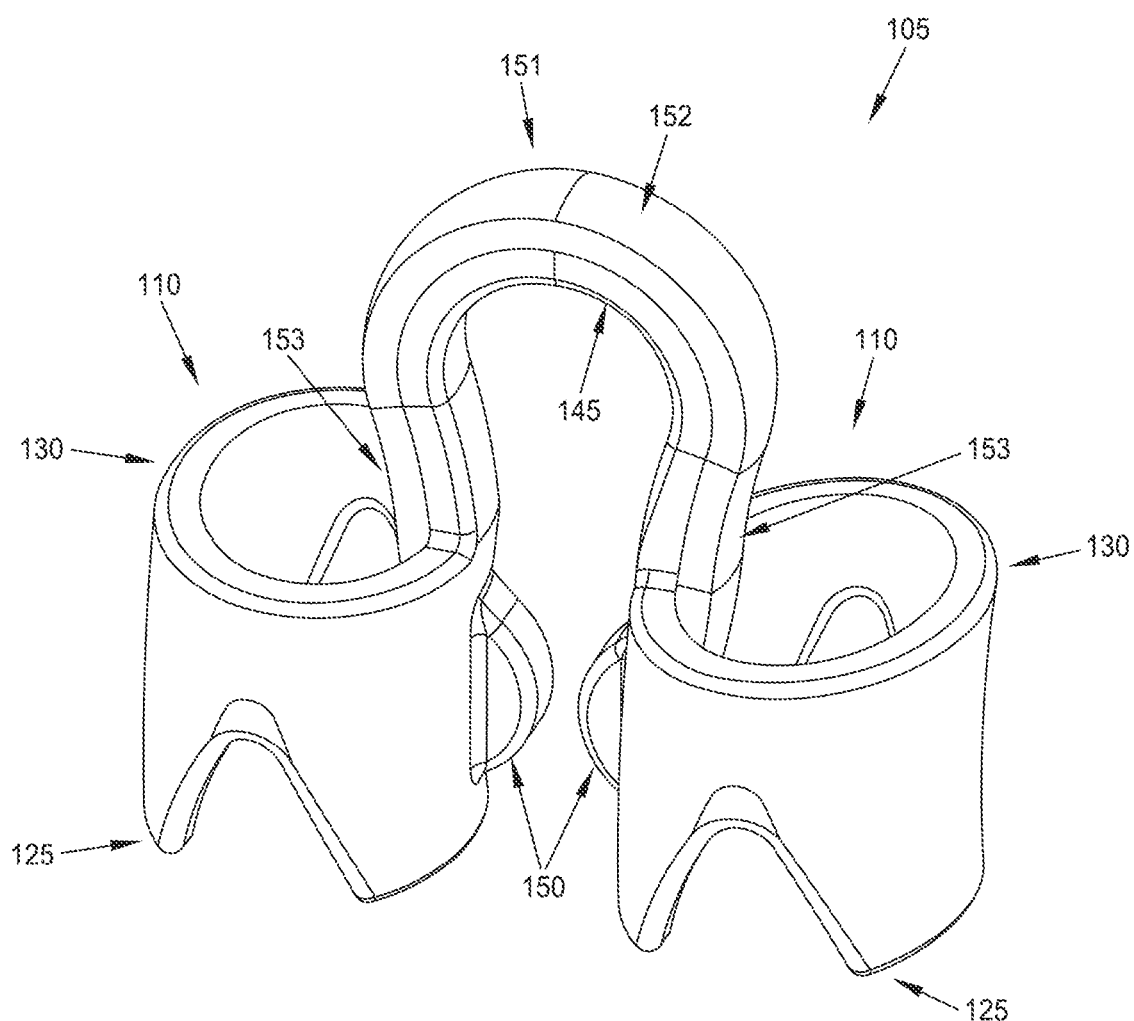
FIGS. 14 and 15 are schematic proximal perspective views of another novel bi-flow nasal stent formed in accordance with the present invention.
Figure 15:
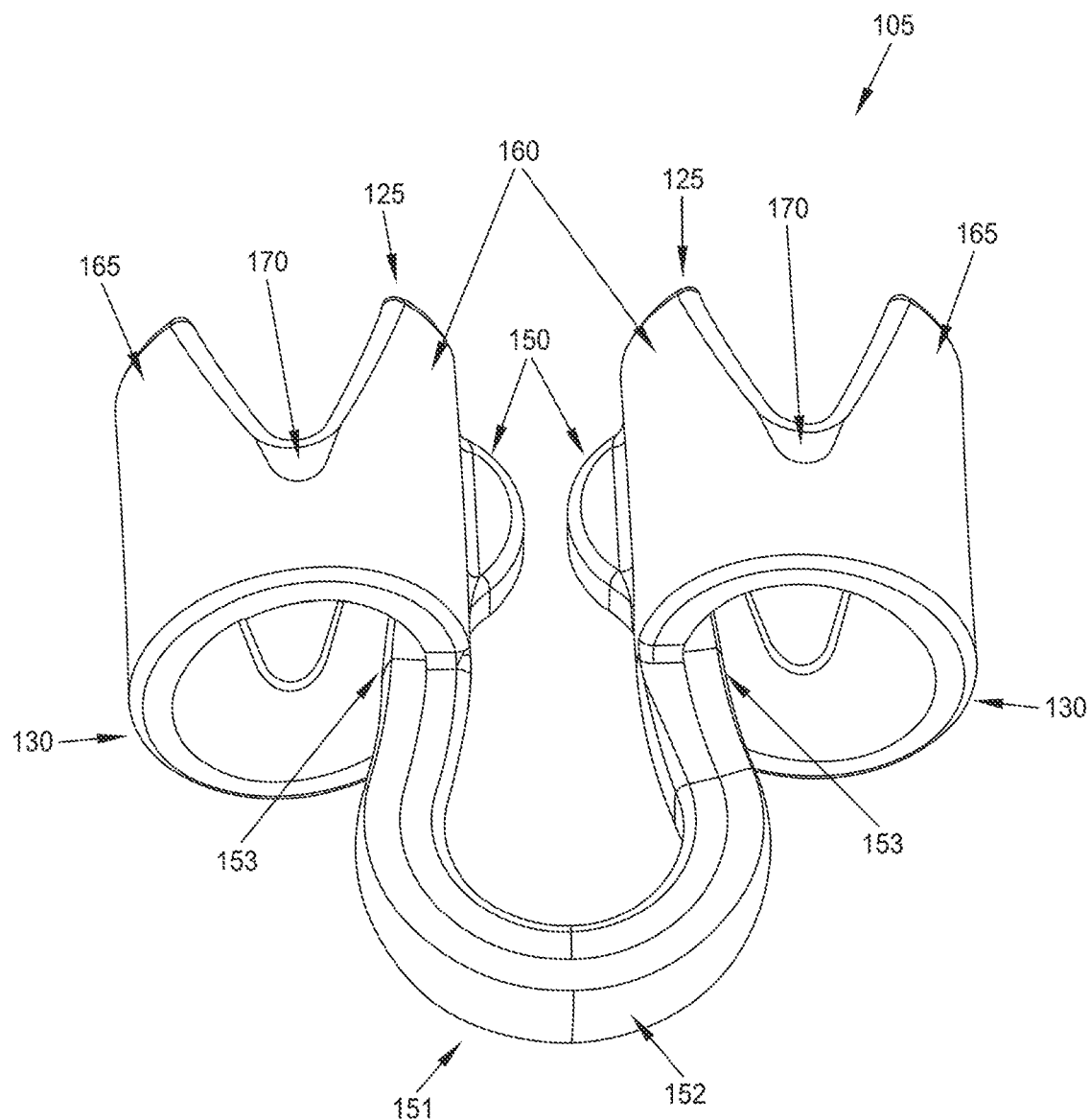
Figure 16:
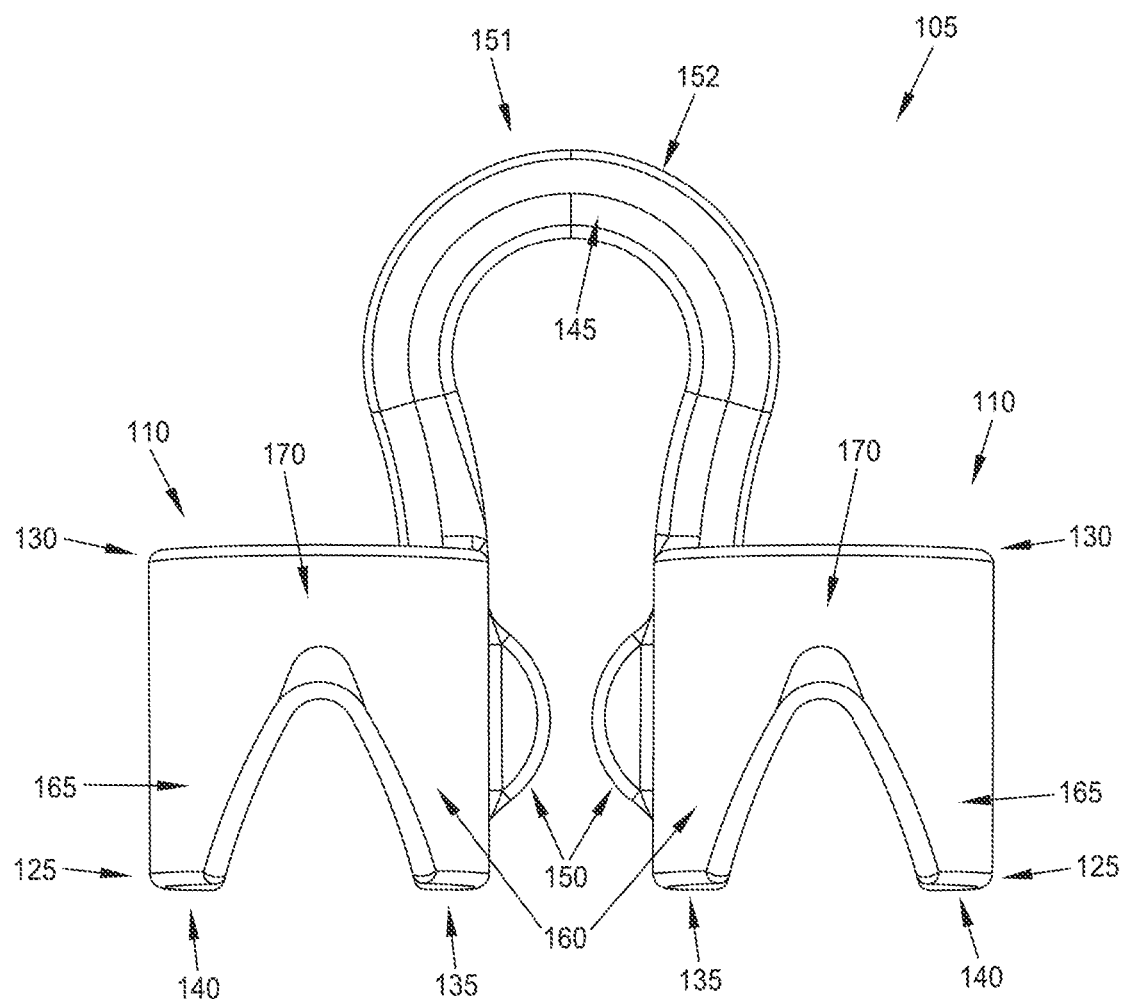
FIG. 16 is a schematic top view of the novel bi-flow nasal stent of FIGS. 14 and 15.
Figure 17:
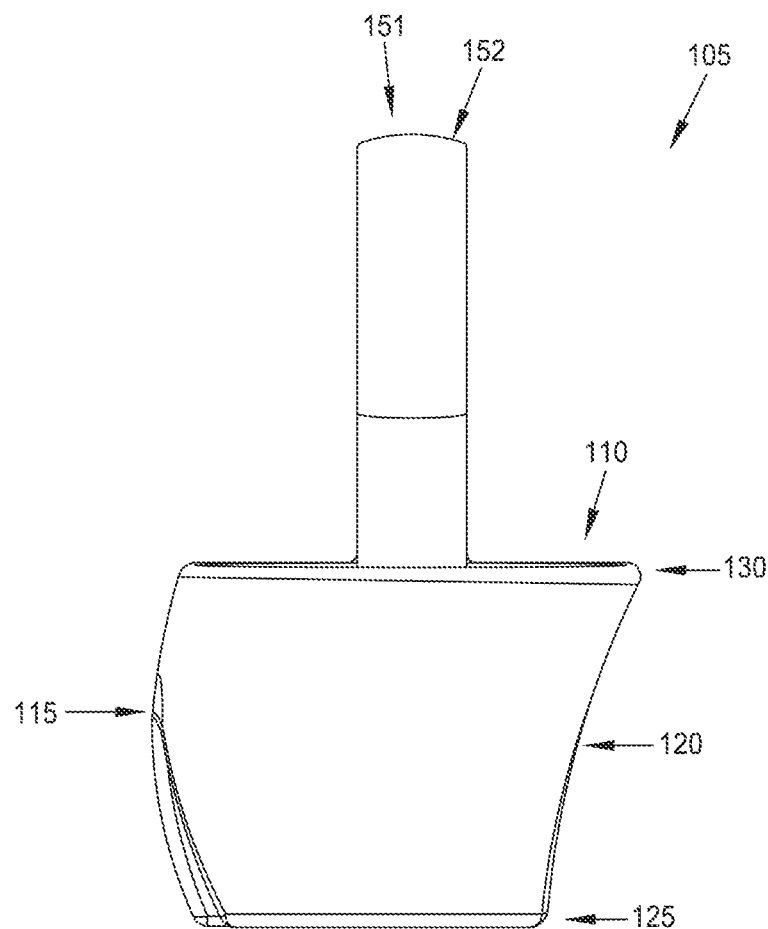
FIG. 17 is a schematic lateral side view of the novel bi-flow nasal stent of FIGS. 14 and 15.
Figure 18:
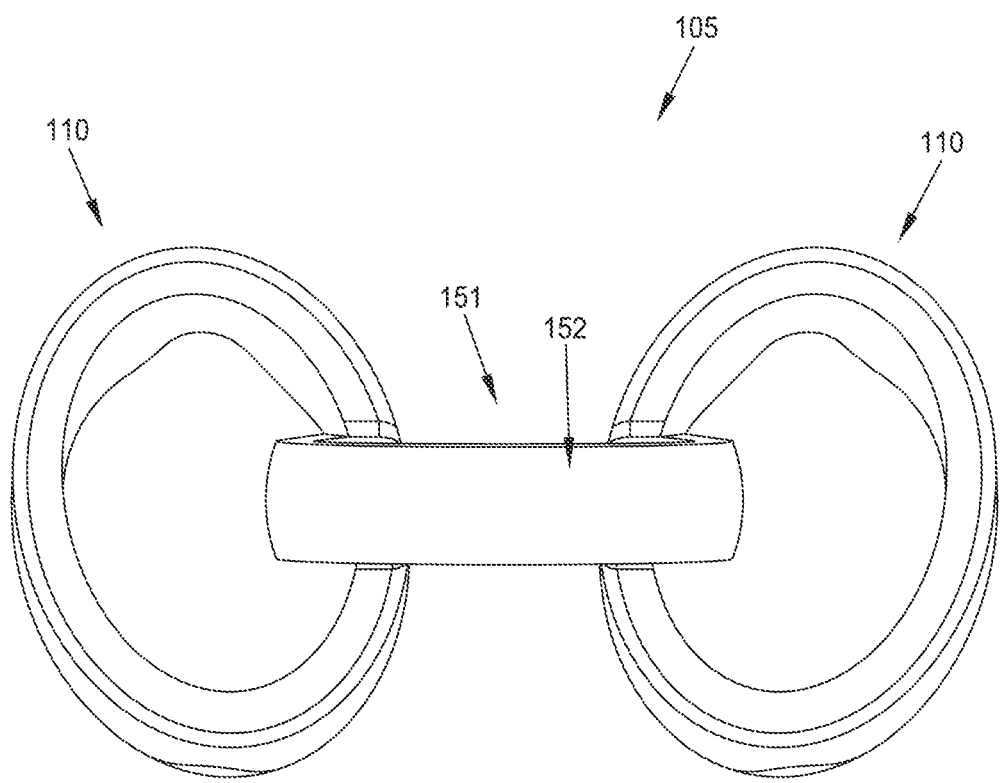
FIG. 18 is a schematic proximal view of the novel bi-flow nasal stent of FIGS. 14 and 15.
Figure 19:
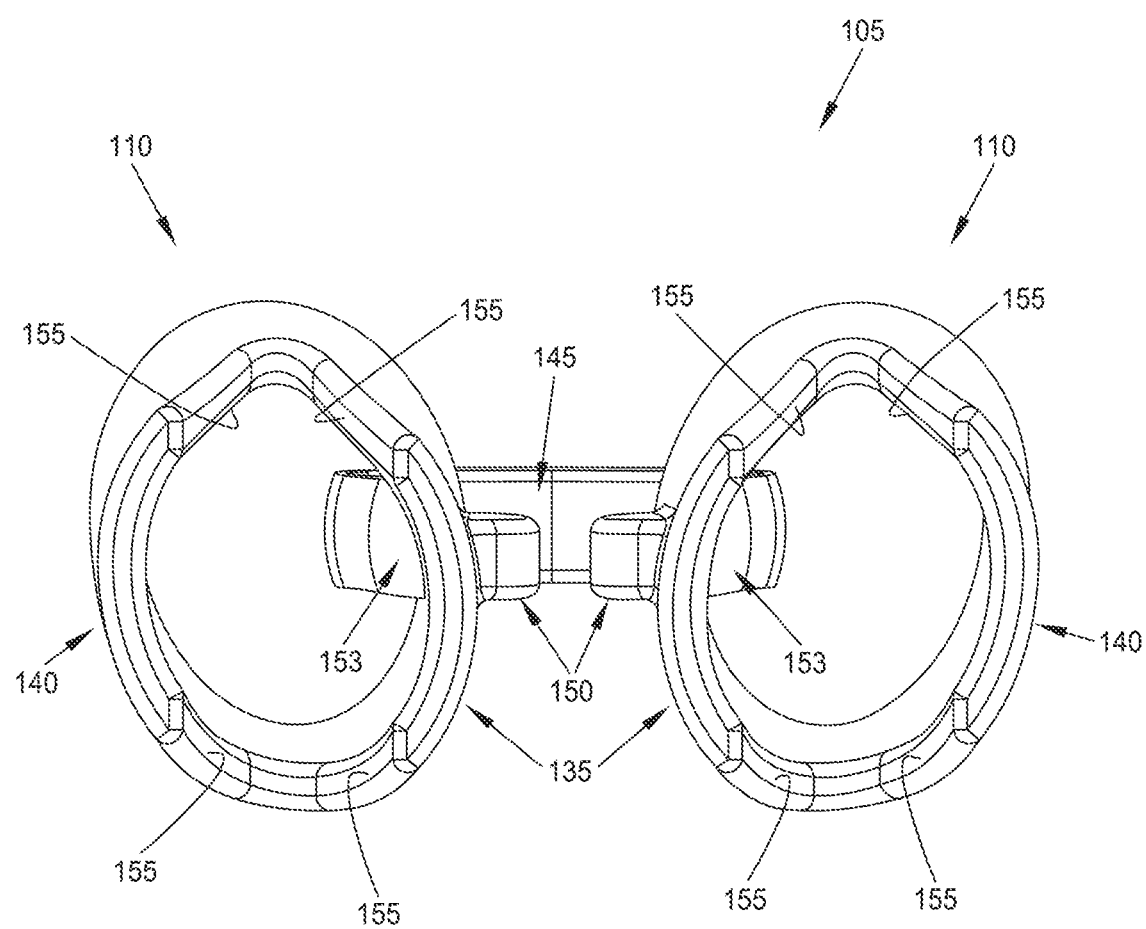
FIG. 19 is a schematic distal view of the novel bi-flow nasal stent of FIGS. 14 and 15.
Figure 20:
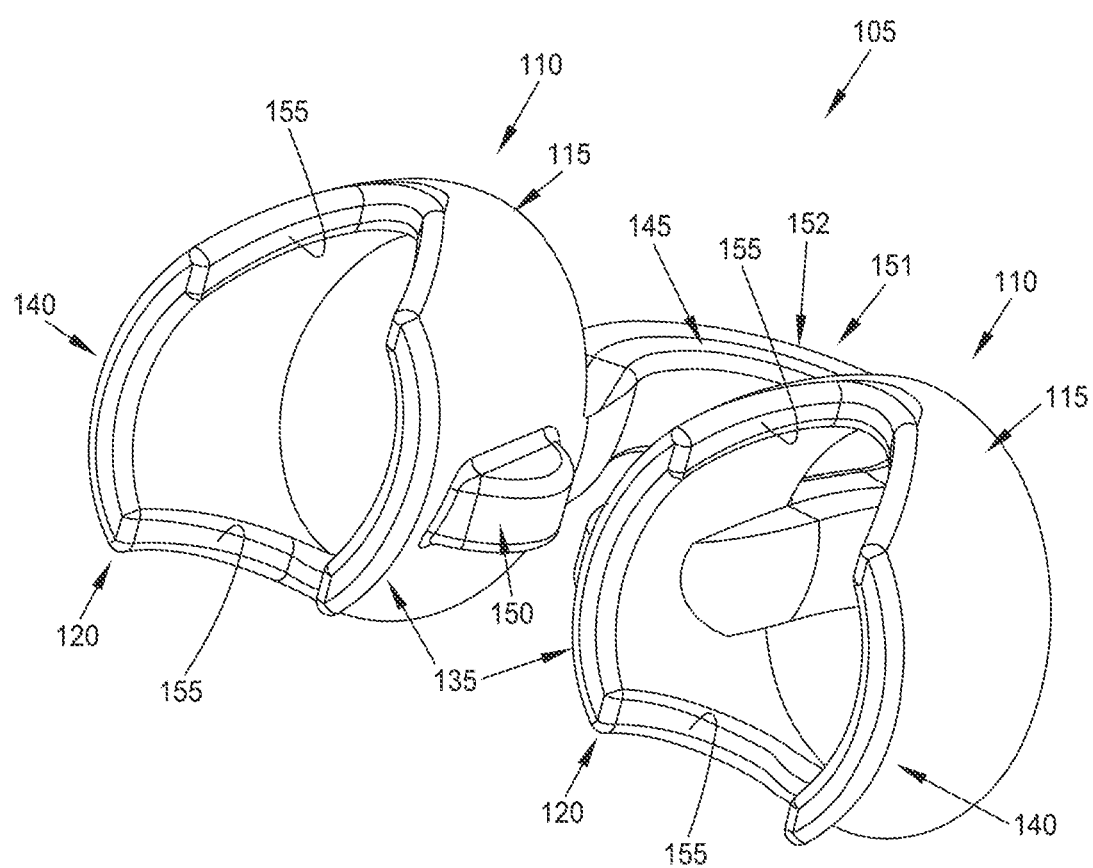
FIGS. 20 and 21 are schematic distal perspective views of the novel bi-flow nasal stent of FIGS. 14 and 15.
Figure 21:
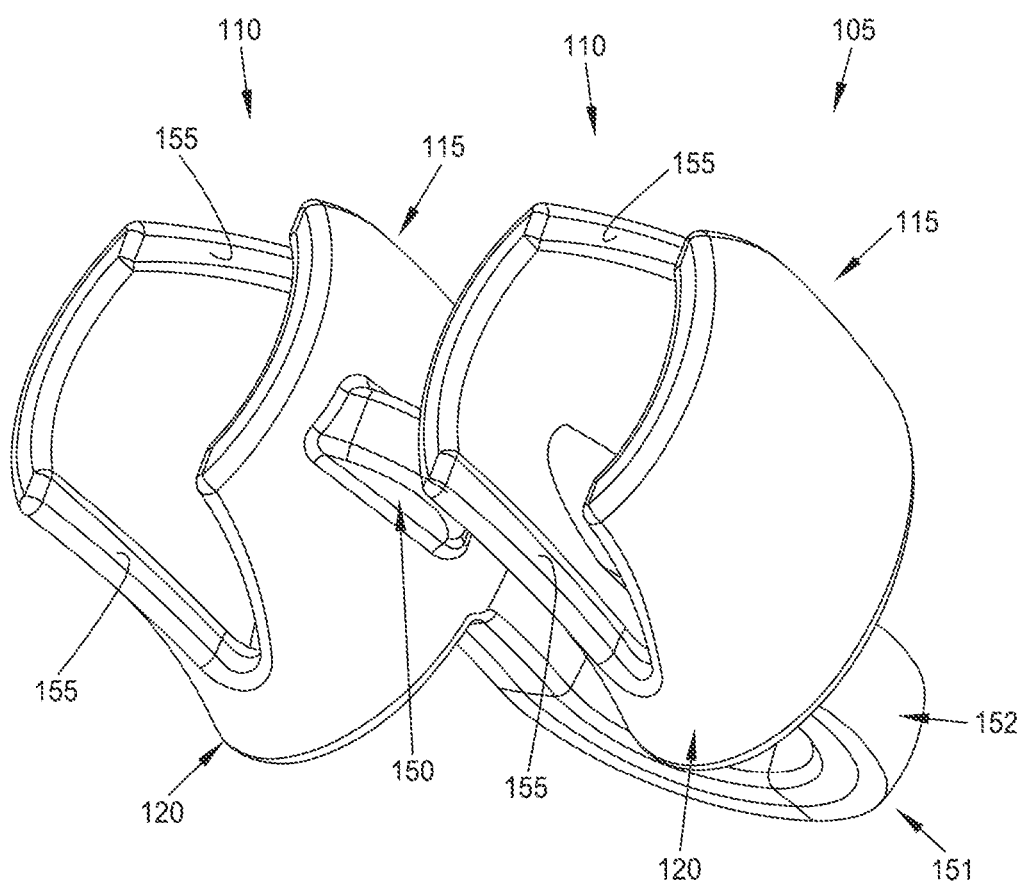
Figure 22:
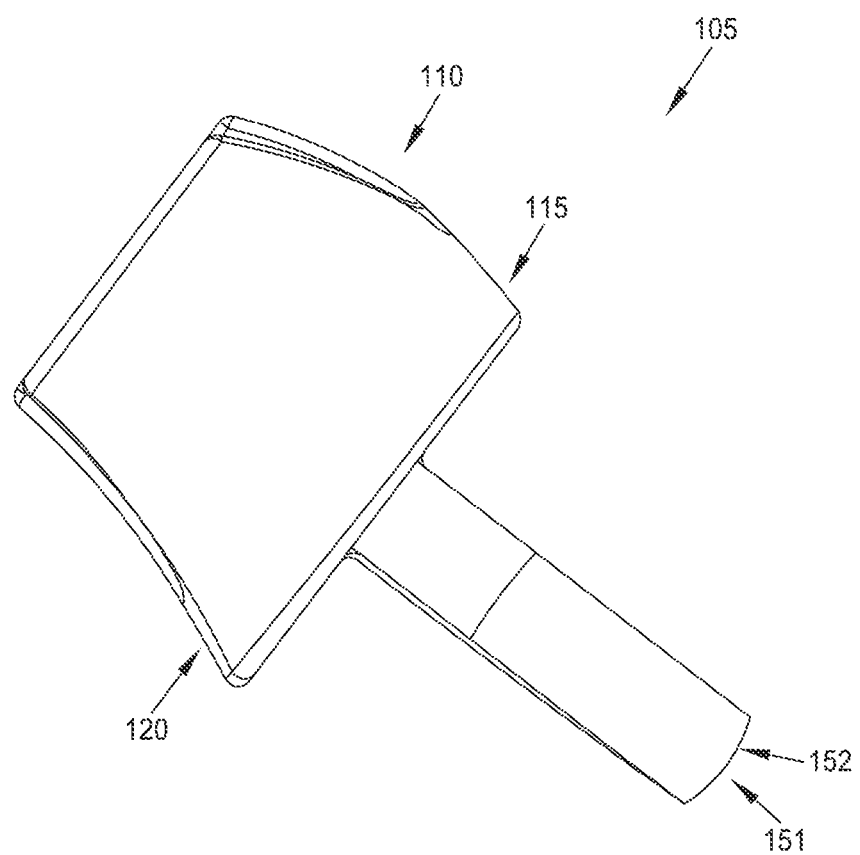
FIG. 22 is another schematic lateral side view of the novel bi-flow nasal stent of FIGS. 14 and 15.

When the novel bi-flow nasal stent 5 is inserted into the nose (FIGS. 12 and 13), tube-like elements 10 sit within the nostrils and bridge 45 fits around the septum. In this position, nubs 50 (if provided) may help hold novel bi-flow nasal stent 5 in position.

During inhalation (see FIG. 12), novel bi-flow nasal stent 5 allows air to flow into the nasal cavity through both upper pathway A and lower pathway B (i.e., the natural pathways for inspired air), since large "V-shaped" cutouts 55 on top portions 15 and bottom portions 20 of tube-like elements 10 allow air to disperse with more verticality.

During exhalation (see FIG. 13), novel bi-flow nasal stent 5 allows air to flow out of the nasal cavity through both upper pathway A and lower pathway B (i.e., the natural pathways for expired air), since large "V-shaped" cutouts 55 on top portions 15 and bottom portions 20 of tube-like elements 10 allow air to enter the tube-like elements at a greater angle.

Thus it will be seen that the unique construction of bi-flow nasal stent 5 (i.e., the provision of the large "V-shaped" cutouts 55, and their specific location relative to the anatomy) provides improved airflow during both inhalation and exhalation.

Significantly, the unique construction features of bi-flow nasal stent 5 also combine to provide effective support for the anatomy while also providing improved wearer comfort, thereby enabling extended periods of wear. For one thing, tube-like elements 10 of bi-flow nasal stent 5 are relatively short and are formed out of a relatively soft elastomeric material, whereby to provide increased user comfort and allow for extended wear. For another thing, the two large "V-shaped" cutouts 55 (which divide the two tube-like elements 10 into medial side portions 60 and lateral side portions 65, with the medial side portions 60 and the lateral side portions 65 being connected by diametrically-opposed spring bridges 70) allow the lateral side portions 65 of tube-like elements 10 to compress towards the medial side portions 60 of tube-like elements 10, whereby to provide effective support for the anatomy while providing improved wearer comfort due to their contouring nature.

Looking next at FIGS. 14-22, there is shown another novel bi-flow nasal stent 105. Novel bi-flow nasal stent 105 generally comprises two tube-like elements 110 each having a top side 115, a bottom side 120, a distal end 125, a proximal end 130, a medial side 135 and a lateral side 140. Novel bi-flow nasal stent 105 further comprises a "U-shaped" bridge 145 which joins tube-like elements 110 on their proximal ends 130. Novel bi-flow nasal stent 105 may also (optionally) comprise nubs 150 on the top, proximal, medial areas of each of the tube-like elements 110 (or at another location on tube-like elements 110). Preferably the two tube-like elements 110, "U-shaped" bridge 145 and nubs 150 (if provided) are all formed integral with one another out of a relatively soft resilient material, e.g., a material soft enough to conform to the anatomy while still providing adequate support for the anatomy.

In addition to the foregoing, bi-flow nasal stent 105 further comprises a spring clip 151 which overlies bridge 145 and extends into the lumens of the two tube-like elements 110. More particularly, spring clip 151 comprises a spring clip bridge 152 and a pair of spring clip legs 153. Spring clip bridge 152 overlies and is adhered to bridge 145, and spring clip legs 153 extend into the lumens of the two tube-like elements 110 and adhere to the side walls of the two tube-like elements 110. Thus, the two tube-like elements 110, the bridge 145 and spring clip 151 together form a single unit, i.e., bi-flow nasal stent 105. Significantly, spring clip legs 153 provide a medially-directed force to the side walls of the two tube-like elements 110, so that when bi-flow nasal stent 105 is inserted into the nostrils of the user, spring clip 151 presses the two tube-like elements 110 against the septum of the user, whereby to help hold bi-flow nasal stent 105 in the nostrils of the user. Note that spring clip bridge 152 sits proximal to bridge 145, and spring clip legs 153 sit internal to the two tube-like elements 110, so that the soft resilient material of bridge 145 and the two tube-like elements 110 sit between spring clip 151 and the tissue of the patient. As a result, spring clip 151 can be formed out of a material which is harder and less conforming than the material which is used to form bridge 145 and the two tube-like elements 110.

Significantly, novel bi-flow nasal stent 105 also comprises a plurality of large "V-shaped" cutouts 155 at distal ends 125 of tube-like elements 110, specifically on the top portions 115 and bottom portions 120 of tube-like elements 110. These large "V-shaped" cutouts 155 are preferably diametrically opposed to one another so as to divide each of the tube-like elements 110 into a medial side portion 160 and a lateral side portion 165, with the medial side portions 160 and the lateral side portions 165 being connected together by a pair of diametrically-opposed connecting elements 170. In one preferred form of the invention, these diametrically-opposed connecting portions 170 act as spring hinges (e.g., resilient living hinges) to allow the medial side portions 160 and the lateral side portions 165 to spring towards and away from one another, whereby to allow the two tube-like elements 110 to conform to the anatomy of the nostrils while still providing adequate support for the anatomy (i.e., adequate support for the nasal valves), with medial side portions 160 applying a gentle force to the septum of the nose and lateral side portions 165 applying a gentle force to the lateral side walls of the nostrils. In this respect it should be appreciated that providing support to the anatomy on the lateral sides of the nostrils is essential for maintaining patency in the nasal channels during respiration. Significantly, with the present invention, when tube-like elements 110 are disposed in the nostrils of the wearer, the lateral side portions 165 can compress towards the medial side portions 160 as needed in order to accommodate the anatomy, but as the lateral side portions 165 are increasingly compressed towards the medial side portions 160, the spring hinges of the diametrically-opposed connecting elements 170 provide the lateral side portions 165 with increasing resistance to the anatomy, whereby to provide excellent anatomical support (i.e., for the nasal valves) and prevent collapse of the nostril walls.

It should be appreciated that each of the tube-like elements 110 is relatively short, e.g., approximately 10 millimeters from distal end to proximal end, with the diametrically-opposed connecting elements 170 being significantly shorter, e.g., approximately 3 millimeters from distal end to proximal end. As a result, tube-like elements 110 of bi-flow nasal stent 105 sit in the wider, less-sensitive proximal portions of the nostrils so as to provide increased user comfort. It should also be appreciated that, as seen in (for example) FIG. 17, tube-like elements 110 have a smaller distal end 125 and a larger proximal end 130, and curved top and bottom sides 115, 120, so as to better fit in the nostrils.

In use, bi-flow nasal stent 105 has its tube-like elements 110 inserted, distal end first, into the nostrils of the patient. As tube-like elements 110 advance into the nostrils of the patient, (i) spring clip legs 153 can flex outwardly so that bi-flow nasal stent 105 can slip over the septum of the nose, and (ii) the lateral and medial side portions 165, 160 of tube-like elements 110 can compress towards one another as needed, so that tube-like elements 110 can seat comfortably and securely in the nostrils. Bi-flow nasal stent 105 can be advanced until bridge 145 approaches or engages the septum of the nose.

When the novel bi-flow nasal stent 105 is inserted into the nose (e.g., in a manner analogous to that shown in FIGS. 12 and 13 with respect to bi-flow nasal stent 5), tube-like elements 110 sit within the nostrils and bridge 145 fits around the septum, with spring clip 151 providing medially-directed forces to help hold tube-like elements 110 against the septum. In this position, nubs 150 (if provided) may help hold novel bi-flow nasal stent 105 in position.

During inhalation, novel bi-flow nasal stent 105 allows air to flow into the nasal cavity through both upper pathway A and lower pathway B (i.e., the natural pathways for inspired air), since large "V-shaped" cutouts 155 on top portions 115 and bottom portions 120 of tube-like elements 110 allow air to disperse with more verticality.

During exhalation, novel bi-flow nasal stent 105 allows air to flow out of the nasal cavity through both upper pathway A and lower pathway B (i.e., the natural pathways for expired air), since large "V-shaped" cutouts 155 on top portions 115 and bottom portions 120 of tube-like elements 110 allow air to enter the tube-like elements at a greater angle.

Thus it will be seen that the unique construction of bi-flow nasal stent 105 (i.e., the provision of the large "V-shaped" cutouts 155, and their specific location relative to the anatomy) provides improved airflow during both inhalation and exhalation.

Significantly, the unique construction features of bi-flow nasal stent 105 also combine to provide effective support for the anatomy while also providing improved wearer comfort, thereby enabling extended periods of wear. For one thing, tube-like elements 110 of bi-flow nasal stent 105 are relatively short and are formed out of a relatively soft elastomeric material, whereby to provide increased user comfort and allow for extended wear. For another thing, the two large "V-shaped" cutouts 155 (which divide the two tube-like elements 110 into medial side portions 160 and lateral side portions 165, with the medial side portions 160 and the lateral side portions 165 being connected by diametrically-opposed spring bridges 170) allow the lateral side portions 165 of tube-like elements 110 to compress towards the medial side portions 160 of tube-like elements 110, whereby to provide effective support for the anatomy while providing improved wearer comfort due to their contouring nature. Additionally, the medially-directed forces provided by spring clip 151 on tube-like elements 110 help bi-flow nasal stent 105 adhere to the septum of the nose.

MODIFICATIONS

It will be understood that many additional changes in the details, materials, steps and arrangements of parts, which have been herein described and illustrated in order to explain the nature of the invention, may be made by those skilled in the art within the principles and scope of the invention as expressed in the appended claims.

What is claimed is:

1. A bi-flow nasal stent comprising:
   first and second tube-like elements; and
   a bridge connecting the first and second tube-like elements;
   wherein each of the first and second tube-like elements comprises a distal end, a proximal end, and a lumen extending therebetween, and further wherein each of the first and second tube-like elements comprises a top side, a medial side, a bottom side, and a lateral side collectively forming the tube-like element;
   wherein first and second V-shaped cutouts are formed at the distal ends of each of the first and second tube-like elements, with the first V-shaped cutout extending proximally from a 12 o'clock position in the top sides of the first and second tube-like elements and the second V-shaped cutout extending proximally from a 6 o'clock position in the bottom sides of the first and second tube-like elements while the bridge connects and extends from the proximal end of the first tube-like element at a 3 o'clock position on the medial side of the first tube-like element to the proximal end of the second tube-like element at a 9 o'clock position on the medial side of the second tube-like element, with the first and second V-shaped cutouts being diametrically opposed to one another so as to divide each of the first and second tube-like elements into a medial side portion and a lateral side portion, with the medial side portion and the lateral side portion being connected together by a pair of diametrically-opposed connecting elements.

2. A bi-flow nasal stent according to claim 1 wherein the first and second tube-like elements comprise a soft resilient material.

3. A bi-flow nasal stent according to claim 1 wherein the distal ends of the first and second tube-like elements are smaller than the proximal ends of the first and second tube-like elements.

4. A bi-flow nasal stent according to claim 1 wherein the bridge is U-shaped.

5. A bi-flow nasal stent according to claim 1 wherein the bridge is formed integral with the first and second tube-like elements.

6. A bi-flow nasal stent according to claim 1 wherein each of the first and second tube-like elements comprises a nub extending radially outboard of the tube-like element.

7. A bi-flow nasal stent according to claim 6 wherein the nubs are formed integral with the first and second tube-like elements.

8. A bi-flow nasal stent according to claim 6 wherein each of the nubs extends radially outward from the point at which the top and medial sides meet.

9. A bi-flow nasal stent according to claim 6 wherein each of the nubs extends radially outward from the medial sides of the first and second tube-like elements.

10. A bi-flow nasal stent according to claim 1 wherein the diametrically-opposed connecting elements act as spring hinges to allow the medial side portions and the lateral side portions to spring towards and away from one another, whereby to allow the first and second tube-like elements to conform to the anatomy of the nostrils, with the medial side portions applying a force to the septum of the nose and the lateral side portions applying a force to the lateral side walls of the nostrils.

11. A bi-flow nasal stent according to claim 1 wherein the diametrically-opposed connecting elements comprise resilient living hinges.

12. A bi-flow nasal stent according to claim 1 wherein each of the first and second tube-like elements is approximately 10 millimeters in length, and further wherein each of the connecting elements is approximately 3 millimeters in length.

13. A bi-flow nasal stent according to claim 1 further comprising a spring clip which overlies the bridge and extends into the lumens of the first and second tube-like elements.

14. A bi-flow nasal stent according to claim 13 wherein the spring clip comprises a spring clip bridge and a pair of spring clip legs, wherein the spring clip bridge overlies and is adhered to the bridge, and further wherein the spring clip legs extend into the lumens of the first and second tube-like elements and adhere to the medial sides of the first and second tube-like elements.

15. A bi-flow nasal stent according to claim 14 wherein the spring clip legs provide a medially-directed force to the medial sides of the first and second tube-like elements, so that when the bi-flow nasal stent is inserted into the nostrils of the user, the spring clip presses the first and second tube-like elements against the septum of the user, whereby to help hold the bi-flow nasal stent in the nostrils of the user.

16. A bi-flow nasal stent according to claim 13 wherein the spring clip bridge sits proximal to the bridge, and the spring clip legs sit internal to the first and second tube-like elements, so that the bridge and the first and second tube-like elements sit between the spring clip and the tissue of the patient.

17. A bi-flow nasal stent according to claim 13 wherein the spring clip is formed out of a material which is harder and less conforming than the material which is used to form the bridge and the first and second tube-like elements.

18. A method for dilating the nostrils of a nose, the method comprising:
   providing a bi-flow nasal stent comprising:
      first and second tube-like elements; and
      a bridge connecting the first and second tube-like elements;
      wherein each of the first and second tube-like elements comprises a distal end, a proximal end, and a lumen extending therebetween, and further wherein each of the first and second tube-like elements comprises a top side, a medial side, a bottom side, and a lateral side collectively forming the tube-like element;
      wherein first and second V-shaped cutouts are formed at the distal ends of each of the first and second tube-like elements, with the first V-shaped cutout extending proximally from a 12 o'clock position in the top sides of the first and second tube-like elements and the second V-shaped cutout extending proximally from a 6 o'clock position in the bottom sides of the first and second tube-like elements while the bridge connects and extends from the proximal end of the first tube-like element at a 3 o'clock position on the medial side of the first tube-like element to the proximal end of the second tube-like element at a 9 o'clock position on the medial side of the second tube-like element, with the first and second V-shaped cutouts being diametrically opposed to one another so as to divide each of the first and second tube-like elements into a medial side portion and a lateral side portion, with the medial side portion and the lateral side portion being connected together by a pair of diametrically-opposed connecting elements;

positioning the medial side portions of the first and second tube-like elements against the medial sides of the nose and positioning the lateral side portions of the first and second tube-like elements against the lateral sides of the nose, with the medial side portions applying a force to the septum of the nose and the lateral side portions applying a force to the lateral side walls of the nose to dilate the nostrils; and permitting inhaled air to flow through the first and second V-shaped cutouts of the first and second tube-like elements and into the nasal cavity and exhaled air to flow out of the nasal cavity and through the first and second V-shaped cutouts of the first and second tube-like elements.

\* \* \* \* \*